(12) United States Patent
Brizzolara et al.

(10) Patent No.: US 6,259,092 B1
(45) Date of Patent: Jul. 10, 2001

(54) THICKNESS DETERMINATION OF CARBONACEOUS OVERLAYERS ON SUBSTRATES OF DIFFERING MATERIAL

(75) Inventors: Robert A. Brizzolara, Beltsville, MD (US); Bruce C. Beard, Hopewell Junction, NY (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/170,041

(22) Filed: Oct. 13, 1998

(51) Int. Cl.[7] .............................. H01J 40/00; H01J 47/00
(52) U.S. Cl. ............................................ 250/305; 250/309
(58) Field of Search .................................... 250/309, 305; 428/627; 427/558

(56) References Cited

PUBLICATIONS

Bruce Beard and Robert Brizzolara, Assessment of overlayer thickness determination model by controlled monolayers, J. Vac. Sci. Techno, A 14, Jan./Feb. 1996.*

\* cited by examiner

Primary Examiner—Jack Berman
Assistant Examiner—Johnnie L Smith, II
(74) Attorney, Agent, or Firm—Howard Kaiser

(57) ABSTRACT

The inventive "Substrate Effect Model" represents an improvement over the "Ebel Model," a conventional XPS-based methodology for determining carbonaceous overlayer thickness. The Ebel Model generally predicts a higher value than the measured value for the ratio of the carbon's C1s electron emission peak to the carbon's CKVV electron emission peak. The invention recognizes the existence and influence of the "Substrate Effect," whereby photoelectrons from the underlying substrate cause additional core-level ionizations in the carbon layer. The failure of the Ebel Model to account for the Substrate Effect is responsible for the variance between Ebel Model prediction and actual x-ray photoelectron spectroscopic measurement. In essence, the invention "corrects" the Ebel Model by accounting for the Substrate Effect. The inventive methodology is applicable not just to carbon but to a diversity of elements which may be found to be included by an overlayer which exists upon a substrate.

18 Claims, 9 Drawing Sheets

| Substrate | Overlayer Thickness: (# Carbons) | Overlayer Thickness: (nm) | $I_{C1s}/I_{CKVV}$ Measured | $I_{C1s}/I_{CKVV}$ Calculated Ebel Model | | Substrate Effect Correction $(1+I_C^e/I_C^x)$ | | $I_{C1s}/I_{CKVV}$ Ebel Model Corrected for Substrate Effect | |
|---|---|---|---|---|---|---|---|---|---|
| | | | | Pure Element | | Pure Element | Oxide | Pure Element | Oxide |
| Si | 10 | 1.28 | 0.68±0.03 | 0.67 | | 1.03 | 1.02 | 0.65 | 0.66 |
| | 12 | 1.53 | 0.73±0.01 | 0.71 | | 1.03 | 1.02 | 0.69 | 0.69 |
| | 16 | 2.05 | 0.75±0.03 | 0.80 | | 1.03 | 1.02 | 0.78 | 0.79 |
| Al | 14 | 1.93 | 0.80±0.01 | 0.79 | | 1.07 | 1.02 | 0.77 | 0.78 |
| Ti | 16 | 2.0 | 0.76±0.04 | 0.79 | | 1.15 | 1.09 | 0.69 | 0.74 |
| Cu | 12 | 1.6 | 0.69±0.06 | 0.72 | | 1.26 | 1.09 | 0.57 | 0.66 |
| Ag | 10 | 1.28 | 0.62±0.04 | 0.67 | | 1.23 | 1.06 | 0.54 | 0.62 |
| Au | 10 | 1.34 | 0.54±0.02 | 0.67 | | 1.29 | | 0.52 | |
| | 13 | 1.67 | 0.56±0.02 | 0.74 | | 1.29 | | 0.57 | |
| | 15 | 1.89 | 0.63±0.03 | 0.77 | | 1.29 | | 0.60 | |
| | 16 | 2.00 | 0.68±0.02 | 0.79 | | 1.29 | | 0.61 | |
| | 17 | 2.11 | 0.65±0.03 | 0.80 | | 1.29 | | 0.62 | |
| | 18 | 2.33 | 0.70±0.06 | 0.83 | | 1.29 | | 0.64 | |

FIG. 4

THICKNESS DETERMINATION OF CARBONACEOUS OVERLAYERS ON SUBSTRATES OF DIFFERING MATERIAL

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to methods, apparatuses and systems for determining one or more physical dimensions of an entity, more particularly for determining the thickness of a thin material overlayer on a solid surface.

There are a number of approaches for determining the thickness of a thin carbon overlayer on a sample surface. Several approaches involve the use of x-ray photoelectron spectroscopy ("XPS").

An example of carbonaceous overlayer thickness determination implementing XPS involves ion beam depth profiling. In accordance therewith, the sample surface is gradually eroded away using an ion beam, and subsequently analyzed with XPS, or Auger electron spectroscopy ("AES"). Performing this process iteratively yields a depth profile of the surface.

Angle-resolved XPS represents another example of XPS-based carbonaceous overlayer thickness determination. According to angle-resolved XPS, photoelectrons are detected at multiple angles with respect to the sample surface. This results in different photoelectron path lengths through the carbon overlayer. From this data, the layer thickness can be determined.

Another XPS-based approach for determining the thickness of a thin carbon overlayer on a sample surface uses two different photoelectron lines with widely differing energies from the same element, in either the substrate or the overlayer. The relative attenuation of the two lines can be used to determine the overlayer thickness.

There are also non-XPS layer thickness techniques, such as ellipsometry.

XPS is a technique by which the elemental composition and chemistry of a solid surface is determined. The surface is illuminated by soft x-rays, resulting in the emission of photoelectrons. XPS is sensitive only to the top few atomic layers of a surface because the photoelectrons have mean free paths of only a few nanometers. XPS can be used to identify the elemental composition of a surface because the photoelectrons have kinetic energies characteristic of the elements in the sample. In addition, XPS can be used to characterize the chemical state of these elements because different chemical states give rise to measurable photoelectron kinetic energy shifts.

The determination of the thickness of thin carbonaceous overlayers on solid surfaces has important technological applications and implications.

For instance, in order to properly determine, using XPS, the composition of a substrate, the presence of an adventitious carbon layer (overlayer) must be accounted for. All samples possess an adventitious carbon layer a few nanometers thick on their surface; however, the adventitious carbon layer on a sample surface can drastically change the quantitation obtained with XPS, because the adventitious carbon layer absorbs photoelectrons from different elements (differing kinetic energies) with different efficiencies. This effect can be corrected for, but only if the thickness of the adventitious carbon layer is known. Since the overlayer thickness is a necessary aspect of this type of substrate composition determination, a speedy and practical method of determining overlayer thickness would be quite beneficial.

Moreover, biofouling of surfaces immersed in seawater is an extremely costly problem for the U.S. Navy. The prevention of such films is of great concern to the U.S. Navy. An effective technique for determining carbonaceous overlayer thickness may help characterize the initial stages of biofilm formation.

Also, there exist certain samples that possess an intentionally formed carbonaceous overlayer on their surface. For example, magnetic disk drives possess a thin lubricating layer on their surface. There is a need in the disk drive industry to measure the thickness of this layer.

Furthermore, layers of small organic molecules on a surface are used as crosslinkers to attach a biological molecule to a surface, as in a biosensor. Layer thickness determination could provide a valuable strategy for characterizing this crosslinking layer.

SUMMARY OF THE INVENTION

In view of the foregoing, it is a principal object of the present invention to provide a methodology for accurately and efficiently determining the thickness of a thin overlayer of a material such as carbon on a solid surface.

The present invention provides a new methodology, based on XPS, for measuring the thickness of a thin material overlayer on an inorganic substrate. The inventive overlayer thickness determination method, apparatus and system are styled herein the "Substrate Effect Model," as distinguished from the overlayer thickness determination methodology which is known as the "Ebel Model."

The Ebel Model, a method proposed by Ebel et al. in the 1980's, provides an important scientific underpinning for the inventive Substrate Effect Model. The Ebel Model provides a mathematical regime which makes use of the C1s photoelectron to CKVV Auger peak area ratio for estimating carbonaceous overlayer thickness on inorganic substrates. In principle, the Ebel Model takes advantage of the differential attenuation of two widely differing kinetic energy photoelectron lines from the same element, viz., carbon. As first proposed by Ebel et al., two electron emission peaks from the carbonaceous overlayer—namely, the C1s electron emission peak and the CKKV electron emission peak—are quite suitable for the purpose of determining carbonaceous overlayer thickness, since these two electron emission peaks are characterized by a large difference between their respective kinetic energies.

The Ebel Model was described in the following paper which is hereby incorporated herein by reference: Ebel, Maria F., M. Schmid, H. Ebel and A. Vogel. "Reduced Thickness of Contamination Layers Determined from C1s is and CKVV-Lines."Journal of Electron Spectroscopy and Related Phenomena 34 (1984): 313–316. Elsevier Science Publishers B. V., Amsterdam, The Netherlands.

The following three papers, each of which is incorporated herein by reference, also discuss use of the C1s photoelectron to CKVV Auger peak area ratio for estimation of carbonaceous overlayer thickness on inorganic substrates:

Reich, T and V. I. Nefedov. "Quantitative XPS Surface Analysis: Correction for Contamination Layer." Journal of Electron Spectroscopy and Related Phenomena 56 (1991): 33–49. Elsevier Science Publishers B. V., Amsterdam, The Netherlands.

Ebel, Maria F., H. Ebel, C. Puchberger and R. Svagera. "On the Energy Dependence of Attenuation Lengths in Hydrocarbon Contaminations," Journal of Electron Spectroscopy and Related Phenomena 57 (1991): 357–372. Elsevier Science Publishers B. V., Amsterdam, The Netherlands.

Weng, L. T., G. Vereecke, M. J. Genet, P. F Rouxhaut, J. H. Stone-Masui, P. Bertrand and W. E. E. Stone. "Quantitative XPS. Part II: Comparison Between Quantitative Approaches for Two Different Spectrometers— Determination of the Contamination-reduced Thickness, Application of the Determined Transmission Functions and Accuracy Achieved." Surface and Interface Analysis 20 (1993): 193–205. John Wiley & Sons, Inc., New York. After introduction of the Ebel Model, experiments by various workers demonstrated that the Ebel Model often significantly underestimated the layer thickness; nevertheless, these experiments were not very accurate. The inventors devised and performed more accurate tests of the Ebel Model; these tests confirmed the previous work demonstrating the Ebel Model to have significant errors.

The inventors subsequently proposed and tested their proposition that a certain physical phenomenon, referred to herein as the "Substrate Effect," is responsible for the inaccuracy in the Ebel Model. The existence of a physical phenomenon like the Substrate Effect was previously known in other contexts, but the effect of such a physical phenomenon on the Ebel Model was first truly appreciated by the inventors.

The inventors constructed the Substrate Effect Model, a mathematical regime which quantifies the Substrate Effect. The inventive Substrate Effect Model was implemented by the inventors in BASIC computer code. The inventors then tested the inventive Substrate Effect Model's predictions against their experimental results and found the agreement to be very good. It is therefore believed by the inventors that the Substrate Effect Model represents a practical and accurate methodology for rendering overlayer thickness determinations.

To test the validity of the inventive Substrate Effect Model, the inventors experimentally measured the C1s/CKVV ratio for carbonaceous overlayers on various substrate materials, and compared the experimental results to the model's predictions. In this regard, hydrocarbon monolayer of precisely controlled thickness were formed on substrates of varying total photoelectron cross-section that would be expected to produce varying levels of the inventive Substrate Effect.

Hence, the inventors have demonstrated that the CKVV signal intensity from a thin carbonaceous overlayer does in fact depend on the substrate underlying the overlayer in the respect that substrate photoelectrons cause photo ionization of carbon atoms in the overlayer; this previously unknown phenomenon is inventively referred to as the Substrate Effect. The inventors have further demonstrated that this dependence of the CKVV signal intensity on the substrate is predictable on the basis of the total photoelectron cross-section and inelastic mean free path of the substrate material. The present invention essentially entails the consideration of the Substrate Effect so as to afford improved accuracy in the determination of overlayer thickness.

The inventive Substrate Effect Model essentially represents an Ebel Model modification which takes the Substrate Effect into consideration. Basically, the crux of the present invention can be stated mathematically as a formulation of the present invention's so-called Substrate Effect Model, wherein the Ebel Model result is said to equal $I_{C1s}/I_{CKVV}^x$, and wherein the inventive Substrate Effect Model is said to equal the Ebel Model result multiplied by the expression $1/(1+(I_{CKVV}^e/I_{CKVV}^x))$.

To summarize, in terms of the development of their work pertaining to the present invention, the inventors have: (i) utilized carbonaceous overlayers of precisely controlled thickness to test the Ebel Model; (ii) determined the substrate photo emission as being the cause of disagreement between the Ebel Model and experiment; (iii) derived the inventive Substrate Effect Model; and, (IV) performed experiments verifying the inventive Substrate Effect Model.

In accordance with many embodiments of the present invention, determination of the thickness of a carbonaceous overlayer which is present on a substrate comprises (a) effectuation of x-ray photoelectron spectroscopy with respect to the carbonaceous overlayer, and (b) evaluation of the ratio of the measured CKVV line intensity to the measured C1s line intensity. The effectuation includes (i) measuring the CKVV electron emission peak, and (ii) measuring the C1s electron emission peak.

The evaluation includes considering the CKVV electron emission peak to be attributable to the combination of (i) direct x-ray excitation of the substrate, and (ii) x-ray excitation of photoelectrons from the substrate.

To elaborate, the Ebel Model accounts for only one of two sources of excitation of the carbon Auger signal. The Ebel Model does take into consideration a first source of excitation, viz., direct x-ray excitation of the substrate; however, the so Ebel Model does not take into consideration a second source of excitation, viz., x-ray excited photoelectrons from the substrate.

The present invention mathematically distinguishes between: (i) the portion of Auger peak intensity corresponding to the first (previously known) source of excitation (which the present invention symbolizes as "$I_{CKVV}^e$"); and, (ii) the portion of Auger peak intensity corresponding to the second (previously unknown) source of excitation (which the present invention symbolizes as "$I_{CKVV}^e$").

The Ebel Model purports to determine the complete quantity of the carbon-1s-to-carbon-KVV line intensity ratio (i.e., the ratio of its C1s photoelectron line intensity to its CKVV Auger line intensity) which is actually measured spectrometrically, viz., $I_{CKVV}^e$. In actuality, however, the Ebel Model determines $I_{C1s}/I_{CKVV}^x$, which is incomplete vis-a-vis $I_{C1s}/I_{CKVV}$ as actually measured spectrometrically.

The Ebel Model considers the $I_{CKVV}^x$ component of $I_{CKVV}$ but fails to consider the $I_{CKVV}^e$ component of $I_{CKVV}$; thus, the Ebel model underestimates the value of the $I_{C1s}/I_{CKVV}$ ratio and overestimates the value of the carbonaceous overlayer thickness. When the inventors conducted experimentation which included measuring $I_{C1s}/I_{CKVV}$ ratios as a function of overlayer thickness, the measured $I_{C1s}/I_{CKVV}$ ratio values were found to be consistently lower than the Ebel Model-predicted $I_{C1s}/I_{CKVV}$ ratio values.

There may be a relationship between overlayer thickness and the amount of discrepancy between the measured $I_{C1s}/I_{CKVV}$ ratio values and the Ebel Model-predicted $I_{C1s}/I_{CKVV}$ ratio values. At one time the inventors thought that this discrepancy may increase with increasing overlayer thickness, but the inventors have since retreated from this conclusion. Nevertheless, the variability of this discrepancy in accordance with overlayer thickness, though uncertain, but is probably both real and small.

In a sense, the present invention redefines the value of $I_{CKVV}$ to equal the sum of two excitational source components; i.e., $I_{CKVV}^x + I_{CKVV}^e$; hence, the complete quantity of the carbon-1s-to-carbon-KVV intensity ratio which is actually measured spectrometrically equals $I_{C1s}/(I_{CKVV}^x + I_{CKVV}^e)$. This recognition of the totality of circumstances pertaining to the carbon Auger signaling in the XPS-based carbonaceous overlayer thickness determination context represents a fundamental concept of the inventive Substrate Effect Model.

In order to determine $I_{C1s}/(I_{CKVV}^x + I_{CKVV}^e)$, the inventors have derived the following equation: $[I_{CKVV}^e/I_{CKVV}^x]$ equals $[\pi N_s \sigma_s^i(h\nu)\lambda_s(E_s^i)]$ divided by $[\sigma_{CKVV}(h\nu)]$. Although the ostensible Ebel Model is $I_{C1s}/I_{CKVV}$, the actual Ebel Model is $I_{C1s}/I_{CKVV}^x$. Therefore, the Ebel Model expression $I_{C1s}/I_{CKVV}^x$ is divided by the invention's corrective expression $(1+I_{CKVV}^e/I_{CKVV}^x)$, thereby obtaining the inventive Substrate Effect Model expression $I_{C1s}/(I_{CKVV}^x + I_{CKVV}^e)$.

In other words, according to the inventive Substrate Effect Model, $$I_{C1s}/I_{CKVV} = I_{C1s}/(I_{CKVV}^x + I_{CKVV}^e) = [I_{C1s}/I_{CKVV}^x] \times [1/(1+I_{CKVV}^e/I_{CKVV}^x)].$$

The Ebel Model equation is conventionally stated as follows:

$$I_{C1s}/I_{CKVV} = \{K(1-\exp[-d/\lambda_C(E_{C1s})\sin\theta])\}/\{(1-\exp[-d/\lambda_C(E_{CKVV})\sin\theta])\}.$$

The Ebel Model equation is inventively restated as follows:

$$I_{C1s}/I_{CKVV}^x = \{K(1-\exp[-d/\lambda_C(E_{C1s})\sin\theta])\}/\{(1-\exp[-d/\lambda_C(E_{CKVV})\sin\theta])\}.$$

Therefore, according to the inventive Substrate Effect Model, the real $I_{C1s}/I_{CKVV}$ equates as follows:

$$I_{C1s}/I_{CKVV} = I_{C1s}/(I_{CKVV}^x + I_{CKVV}^e) = [I_{C1s}/I_{CKVV}^x]/[(1+I_{CKVV}^e/I_{CKVV}^x)] =$$
$$\{K(1-\exp[-d/\lambda_C(E_{C1s})\sin\theta])\}/\{(1-\exp[-d/\lambda_C(E_{CKVV})\sin\theta])(1+I_{CKVV}^e/I_{CKVV}^x)\}.$$

The carbonaceous overlayer thickness d can be inventively obtained by solving for d in the abovesaid equations.

It is thus seen that the inventive Substrate Effect Model alters the functional relationship between carbonaceous overlayer thickness d and the carbon-1s-to-carbon-KVV ratio $I_{C1s}/I_{CKVV}$ so as to obtain a value for carbonaceous overlayer thickness d which normally runs higher than which is obtained by the Ebel Model. Conversely expressed, the inventive Substrate Effect Model alters the functional relationship between carbonaceous overlayer thickness d and the carbon-1s-to-carbon-KVV ratio $I_{C1s}/I_{CKVV}$ so as to obtain a value for the carbon-1s-to-carbon-KVV ratio $I_{C1s}/I_{CKVV}$ which normally runs lower than that which is obtained by the Ebel Model.

The present invention incorporates established Ebel Model-related principles into a new and improved methodology for determining carbonaceous overlayer thickness. The Ebel Model provides basic information but is inventively compensated for. Typical inventive practice involves a procedure which includes performance of acts generally as hereindescribed in the next several paragraphs.

The K constant is empirically determined by measuring the $I_{C1s}/I_{CKVV}$ ratio on a specimen of bulk carbon.

The sample is empirically surveyed under the same conditions under which the K constant will be or has been empirically determined.

Based on the empirical survey, the approximate composition of the sample is identified.

Based on the sample composition thus identified, the value of $I_{CKVV}^e/I_{CKVV}^x$ is calculated.

Focusing on the CKVV and C1s areas in the survey, the $I_{C1s}/I_{CKVV}$ ratio is measured, and then normalized using the K constant which has been empirically determined.

Using the inventive Substrate Effect Model and applying the calculated value of $I_{CKVV}^e/I_{CKVV}^x$, a relationship is established (which can be manifested, e.g., graphically or tabularly) between the $I_{C1s}/I_{CKVV}$ ratio and the carbonaceous overlayer thickness.

The overlayer thickness of the sample is ascertained (e.g., interpolated or extrapolated) by associating the measured, normalized value of the $I_{C1s}/I_{CKVV}$ ratio with the relationship established, pursuant to the inventive Substrate Effect Model, between the $I_{C1s}/I_{CKVV}$ ratio and overlayer thickness.

The inventive method of carbonaceous overlayer thickness determination on a solid substrate affords a number of advantages over existing methods. The inventive method is nondestructive, unlike ion beam depth-profiling that requires erosion of the sample surface. The inventive method is very simple and fast, unlike ion-beam depth profiling and angle resolved XPS that require acquisition of multiple XPS spectra and complex data analysis. The inventive method does not require knowledge of obscure physical quantities regarding the carbonaceous overlayer, which often are not known, such as the dielectric constant, as in ellipsometry.

This invention has applicability in diverse situations, both wherein the presence of the thin carbonaceous overlayer is adventitious as well as wherein the presence of the thin carbonaceous overlayer is deliberate. Notable among the multifarious applications of this invention are: the compensation for adventitious carbon layer thickness in connection with determination of substrate composition using XPS; the characterization of biological films on surfaces; and, the evaluation of lubricant thickness on magnetic disk drives.

Of particular note, many embodiments of the present invention afford improved accuracy in the correction of the presence of an adventitious carbonaceous overlayer in the quantitative analysis of XPS data. This correction can be performed using simple computer code and existing survey scan data, provided calibration data of bulk carbon (e.g., high density polyethylene) has been acquired under the same instrumental conditions. Accordingly, the present invention will make possible more accurate quantitative analysis of XPS data.

Potentially, the present invention can be applied to overlayers of materials other than those containing carbon, provided the overlayer-possessed photo emission or Auger lines are sufficiently widely separated in kinetic energy. XPS can be inventively implemented to measure the thickness of thin overlayers of diverse compositions. In typical inventive practice, the thin overlayer is of nanometer-scale thickness. Certainly, many preferred inventive embodiments utilize the carbon 1s and carbon KVV peak intensities for measuring the thickness of a thin carbonaceous overlayer on a substrate. Nevertheless, the present invention is applicable not only to carbon-containing overlayer compositions but also to many other element-containing overlayer compositions.

For instance, many materials of technological import possess a thin oxide overlayer. The inventive methodology can be used to determine the thickness of such an oxide overlayer by employing two lines, as follows: (i) the Auger emission peak, viz., O(KVV); and (ii) either the O(1s) emission peak or the O(2s) emission peak. In other words, the emission peak pair which will be selected will be either (i) O(KVV) and O(1s), or (ii) O(KVV) and O(2s). This selection of two lines will be based on their intensity and their separation in kinetic energy. The peak intensity of a line will depend on the sample, since the thickness of the oxide overlayer will affect the peak intensity. Thicker oxide overlayers will typically have greater peak intensities associated therewith.

In inventive practice, generally, the criteria for selection of two lines will include (i) the intensity of the lines and (ii) the separation of the lines in kinetic energy. Generally, the peak intensity of a line will be sample-dependent, with the peak intensity varying in accordance with the thickness of the overlayer; this is, the thicker the overlayer, the greater the peak intensity.

A question arises as to how much of an element must be included in the overlayer in order that this invention can be effectively practiced by availing of such element. The inventors believe that such a question does not admit of mathematical thresholding, such as in terms of compositional percentage.

Clearly, an overlayer which is predominately a particular element will normally lend itself to inventive practice with respect to such element. The Ebel Model was founded on a presumption that carbon was the predominant substance in the overlayer. Similarly, inventive testing was performed on carbonaceous overlayers which were predominately carbon; indeed, the carbonaceous overlayers used in inventive experimentation essentially consisted of carbon.

An inventive rule of thumb is: The present invention can be applied to an element which is sufficiently prevalent in the overlayer to give rise to sufficiently appreciable signaling, in terms of peak intensity, of two sufficiently distinct lines (one Auger, one non-Auger), through implementation of equipment which is available to the inventive practitioner.

Whether or not an element is prevalent enough in an overlayer may depend not only on the percentage (e.g., by mass or weight) of the element which is included in the overlayer, but also on the thickness of the overlayer. Assuming that a substance is (to at least a substantial degree) distributed in a uniform or homogeneous fashion in an overlayer, the amount of a substance which is distributed in an overlayer—and hence, a peak intensity associated with that element—is basically a function of the overlayer's thickness. Generally speaking, then, the peak intensity increases in accordance with increasing overlayer thickness.

Regardless of the overlayer composition—more specifically, regardless of which element is being subjected to XPS—the inventive principles basically still obtain. The invention accounts for two sources of excitation of the elemental Auger signal: (i) direct x-ray excitation of the substrate (which the Ebel Model accounts for) and (ii) x-ray excited photoelectrons from the substrate (which the Ebel Model fails to accounts for). Fundamentally, according to the inventive Substrate Effect Model, the invention recognizes the totality of circumstances pertaining to the element's Auger signaling in the context of XPS-based elemental overlayer thickness determination.

The inventive methodology for determining elemental overlayer thickness in general compensates for the Ebel Model similarly as does the inventive methodology for determining carbonaceous overlayer thickness in particular. Inventive practice in connection with any overlayer element involves performance of acts analogous to those specifically disclosed herein in connection with the overlayer element carbon.

The inventive mathematical relationships for the "general case" parallel those for the "specific case" wherein there is a carbonaceous overlayer upon a substrate. That is to say, equations disclosed herein for carbonaceous overlayers can be generalized for any elemental overlayer. In inventive practice, generally, the inventive methodology utilizes a non-Auger peak intensity (designated herein "$I_{Znl}$") and an Auger peak intensity (designated herein "$I_{Z(A)}$"), each pertaining to the same particular element (designated herein "Z"). "Znl" refers to a non-Auger electron emission peak for element Z; typically, "nl" will describe a numerical symbol followed by a letter symbol. "Z(A)" refers to an Auger electron emission peak for element Z.

For any element Z which an overlayer includes and which admits of XPS, the present invention mathematically distinguishes between: (i) the portion of Auger peak intensity corresponding to direct x-ray excitation of the substrate (designated herein "$I_{Z(A)}^x$"); and, (ii) the portion of Auger peak intensity corresponding to x-ray excited photoelectrons from the substrate (designated herein "$I_{Z(A)}^e$"). The value of $I_{Z(A)}$ is inventively redefined to equal the sum of two excitational source components; that is, $I_{Z(A)} = I_{Z(A)}^x + I_{Z(A)}^e$. Accordingly, the complete quantity of the elemental-nl-to-elemental-(A) intensity ratio which is actually measured spectrometrically equals $I_{Znl}/(I_{Z(A)}^x + I_{Z(A)}^e)$.

The following inventively derived equation is inventively used in order to determine $I_{Znl}/(I_{Z(A)}^x + I_{Z(A)}^e)$: $[I_{Z(A)}^e/I_{Z(A)}^x]$ equals $[\pi N_s \sigma_s^i(h\nu)\lambda_s(E_s)\sigma_{Z(A)}(E_s^i)]$ divided by $[\sigma_{Z(A)}(h\nu)]$. The "ostensible" Ebel Model for the specific case of carbon, $I_{C1s}/I_{CKVV}$, can be reformulated for the general case of any element as $I_{Znl}/I_{Z(A)}$. Thus, the "actual" Ebel Model for the general case is $I_{Znl}/I_{Z(A)}^x$. Therefore, the Ebel Model expression $I_{Znl}/I_{Z(A)}^x$ is divided by the invention's corrective expression $(1+I_{Z(A)}^e/I_{Z(A)}^x)$, thereby obtaining the inventive Substrate Effect Model expression $I_{Znl}/(I_{Z(A)}^x+I_{Z(A)}^e)$.

In other words, for any overlayer element Z, according to the inventive Substrate Effect Model, $$I_{Znl}/I_{Z(A)} = I_{Znl}/(I_{Z(A)}^x+I_{Z(A)}^e) = [I_{Znl}/I_{Z(A)}^x] \times [1/(1+I_{Z(A)}^e/I_{Z(A)}^x)].$$

The Ebel Model equation can be expressed for the general case as follows:

$$I_{Znl}/I_{Z(A)} = \{K(1-\exp[-d/\lambda_Z(E_{Znl})\sin\theta])\}/\{(1-\exp[-d/\lambda_Z(E_{Z(A)})\sin\theta])\}.$$

The above-generalized Ebel Model equation can be inventively restated as follows:

$$I_{Znl}/I_{Z(A)}^x = \{K(1-\exp[-d/\lambda_Z(E_{Znl})\sin\theta])\}/\{(1-\exp[-d/\lambda_Z(E_{Z(A)})\sin\theta])\}.$$

Therefore, according to the inventive Substrate Effect Model, the real $I_{Znl}/I_{Z(A)}$ equates as follows:

$$I_{Znl}/I_{Z(A)} = I_{Znl}/(I_{Z(A)}^x+I_{Z(A)}^e) = [I_{Znl}/I_{Z(A)}^x]/[(1+I_{Z(A)}^e/I_{Z(A)}^x)] =$$

$$\{K(1-\exp[-d/\lambda_Z(E_{Znl})\sin\theta])\}/(\{1-\exp[-d/\lambda_Z(E_{Z(A)})\sin\theta])(1+I_{Z(A)}^e/I_{Z(A)}^x)\},$$

wherein: $I_{Znl}$ is the elemental nl intensity; $I_{Z(A)}$ is the elemental (A) intensity; d is the thickness of the elemental overlayer; $\lambda_Z(E_{Znl})$ is the inelastic mean free path of the elemental nl photoelectrons in the element; $\lambda_Z(E_{Z(A)})$ is the inelastic mean free path of the elemental Auger electrons in the element; $\theta$ is the angle of emission of photoelectrons with respect to the plane of the substrate; K is a constant which is equal to the measured $I_{Znl}/I_{Z(A)}$ for an infinitely thick elemental sample; $I_{Z(A)}^x$ is the portion of the elemental (A) intensity corresponding to direct x-ray excitation of the substrate; $I_{Z(A)}^e$ is the portion of the elemental (A) intensity corresponding to photoelectron excitation from said substrate; $[I_{Z(A)}^e/I_{Z(A)}^x]$ equals $[\pi N_s \sigma_s^i(h\nu) \lambda_s(E_s^i)]$ divided by

[$\sigma_{Z(A)}(h\nu)$]; $N_s$ is the number of substrate atoms/cm$^3$; $\sigma_s^i(h\nu)$ is the cross-section for photoelectron emission from the ith core level of the substrate; $\lambda_s(E_s^i)$ is the inelastic mean free path of substrate photoelectrons from the ith core level of the substrate; $\sigma_{Z(A)}(E_s^i)$ is the cross-section for elemental Augers emission upon bombardment by electrons from the ith core level of the substrate; and, $\sigma_{Z(A)}(h\nu)$ is the cross-section for elemental Auger emission by x-ray excitation.

The elemental overlayer thickness d can be inventively obtained by solving for d in the above said equations.

It is thus seen that, for the general case, the inventive Substrate Effect Model alters the functional relationship between elemental overlayer thickness d and the elemental-nl-to-elemental-(A) ratio $I_{Znl}/I_{Z(A)}$ so as to obtain a value for elemental overlayer thickness d which normally runs higher that that which is obtained through generalization (to any overlayer element) of the Ebel Model. Conversely expressed, the inventive Substrate Effect Model alters the functional relationship between elemental overlayer thickness d and the elemental-nl-to-elemental-(A) ratio $I_{Znl}/I_{Z(A)}$ so as to obtain a value for the elemental-nl-to-elemental-(A) ratio $I_{Znl}/I_{Z(A)}$ which normally runs lower that that which is obtained through generalization (to any overlayer element) of the Ebel Model.

Notable is the following unpublished paper, authored by the inventors and submitted for publication on or about Mar. 13, 1998, which discloses various aspects of the present invention: Brizzolara, Robert A., Bruce C. Beard. "Substrate Photoelectron Enhancement of Carbonaceous Overlayer Auger Emission: Effect of the Substrate on Carbon Overlayer Thickness Determination in XPS." Submitted Mar. 13, 1998, not yet accepted for publication. *Surface and Interface Analysis*. John Wiley & Sons, Inc., New York.

BRIEF DESCRIPTION OF THE DRAWINGS

In order that the present invention may be clearly understood, it will now be described by way of example, with reference to the accompanying drawings, wherein like numbers indicate the same or similar components, and wherein:

As shown in FIG. 1, C=carbonaceous overlayer; S=substrate; Z=z direction (normal to sample surface); h$\nu$=incident x-ray flux; $I_C^e$=carbon KVV electrons excited by x-rays; $I_C^e$=carbon KVV electrons excited by substrate photoelectrons; and, $n_s^i$=substrate photoelectrons.

FIG. 4 is a table which summarizes Substrate Effect data (both experimental data and model data).

DETAILED DESCRIPTION OF THE INVENTION

Derivation of the Substrate Effect Model

Figure 1:
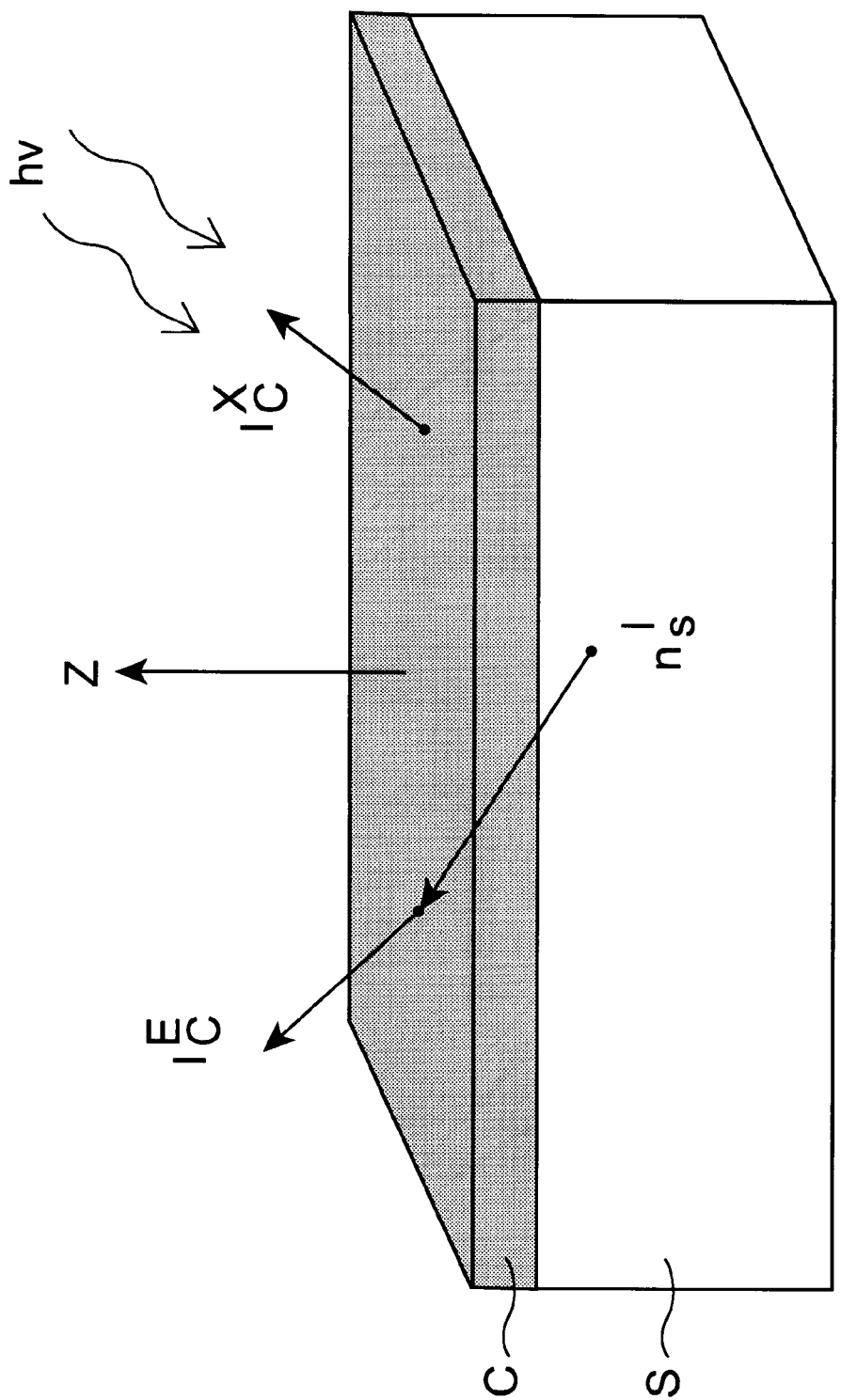
FIG. 1 is a diagrammatic perspective view of sample geometry showing a carbonaceous overlayer of thickness d on a substrate composed of a different material.

Referring now to FIG. 1, the objective is to determine the ratio of C1s to CKVV emission intensity from a sample. The geometry of the sample is depicted in FIG. 1. The sample comprises a thin (0.5 to 5 nm) carbon overlayer C of thickness d supported by a substrate S of some element. Substrate S is very thick compared to overlayer C.

We start with the Ebel model that gives an expression for $I_{C1s}/I_{CKVV}$ as:

$$I_{C1s}/I_{CKVV} = K(1-\exp[-d/\lambda_C(E_{C1s})\sin\theta])/(1-\exp[-d/\lambda_C(E_{CKVV})\sin\theta]) \quad (1)$$

where d is the overlayer thickness, $\lambda_C(E_{C1s})$ is the inelastic mean free path of carbon 1s photoelectrons in carbon, $\lambda_C(E_{CKVV})$ is the inelastic mean free path of carbon Auger electrons in carbon, $\theta$ is the angle of emission of photoelectrons with respect to the sample surface plane, and K is a constant which is equal to the measured $I_{C1s}/I_{CKVV}$ for an infinitely thick carbon sample.

The inventors tested the Ebel Model and found its $I_{C1s}/I_{CKVV}$ prediction is consistently low for certain substrates. See Beard, Bruce C. and Robert A. Brizzolara. "Assessment of Overlayer Thickness Determination Model by Controlled Monolayer." Journal of Vacuum Science and Technology A 14(1) (Jan/Feb 1996): 89–94, incorporated herein by reference.

The inventors subsequently determined that this error associated with the Ebel Model is due to the Substrate Effect. The Substrate Effect arises from the fact that the carbon Auger signal has two sources of excitation. The first source is direct x-ray excitation ($I_{CKVV}^x$) which is accounted for in the Ebel Model. The second source is x-ray excited photoelectrons from the substrate, ($I_{CKVV}^e$), not accounted for in the Ebel model.

Thus, the quantity determined in the Ebel Model is actually $I_{C1s}/I_{CKVV}^x$. As disclosed herein, the inventors have determined $I_{C1s}/(I_{CKVV}^x + I_{CKVV}^e)$, which is the quantity actually measured by the spectrometer.

To this end, the inventors have derived $I_{CKVV}^e/I_{CKVV}^x$, and then multiplied $I_{C1s}/I_{CKVV}^x$, which is the Ebel Model result, by $(1/(1+I_{CKVV}^e/I_{CKVV}^x))$.

The ratio $I_{CKVV}^e/I_{CKVV}^x$ is:

$$\frac{I_{CKVV}^e}{I_{CKVV}^x} = \frac{\pi N_s \sigma_s^i(h\nu) \lambda_s(E_s^i) \sigma_{CKVV}(E_s^i)}{\sigma_{CKVV}(h\nu)} \quad (2)$$

This quantity is summed over all substrate photoelectron and Auger transitions.

The following derivation of equation (2), which includes equations (3) through (9), is appropriately considered as containing two parts, viz., (a) carbon Auger emission via x-ray excitation, and (b) carbon Auger emission via excitation by substrate photoelectrons.

(a) Carbon Auger Emission via X-ray Excitation

The x-ray excited carbon Auger emission from the sample depicted in FIG. 1 is:

$$I_{CKVV}^x = \quad (3)$$

$$\sigma_{CKVV}(h\nu) D(E_{CKVV}) T(E_{CKVV}) J_0 N_C \int_{z=0}^{d} \exp[-z/\lambda_C(E_{CKVV}) \sin\theta_C] dz$$

where $\sigma_{CKVV}(h\nu)$ is the cross-section for carbon Auger emission by x-ray excitation, $D(E_{CKVV})$ is the efficiency of the electron detector, $T(E_{CKVV})$ is the analyzer transmission function, $J_0$ is the x-ray flux, $N_C$ is the number of carbon atoms per cm$^3$, $\lambda_C(E_{CKVV})$ is the inelastic mean free path of carbon Auger electrons in carbon, $\theta_C$ is the angle of emission of carbon Auger electrons relative to the sample surface, $E_{CKVV}$ is the kinetic energy of carbon Auger electrons, and hv is the x-ray energy, and z is the depth into the sample with z=0 taken to be the surface of the carbonaceous overlayer. See Briggs, D. and M. P. Seah, eds., *Practical Surface Analysis by Auger and X-ray Photoelectron Spectroscopy*, John Wiley & Sons, Ltd., 1983, p 197, equation (5.14), incorporated herein by reference.

Performing the z-integration yields:

$$I^X_{CKVV} = \sigma_{CKVV}(hv)D(E_{CKVV})T(E_{CKVV})J_0 \qquad (4)$$
$$N_C\lambda_C(E_{CKVV})\sin\theta_C[1-\exp[-d/\lambda_C(E_{CKVV})\sin\theta_C]]$$

(b) Carbon Auger Emission via Excitation by Substrate Photoelectrons

To determine the intensity of carbon Auger emission from substrate photoelectron excitation, the flux of substrate photoelectrons crossing the substrate-carbon interface into the carbon overlayer will be used as a "source" term in an expression for carbon Auger emission via excitation by substrate photoelectrons. In this derivation, it will be assumed the substrate is composed of a single element of infinite thickness relative to the electron emission path lengths. We start with the number of substrate photoelectrons from the ith energy level crossing the substrate/carbon interface at an angle θ and φ:

$$n^i_s = N_s J_0 \sigma^i_s(hv) \int_{z=0}^{\infty} \exp[-z/\lambda_s(E^i_s)\sin\theta_s]dz \qquad (5)$$

where $N_s$ is the number of substrate atoms/cm³, as $\sigma^i_s(hv)$ is the cross-section for photoelectron emission from the ith substrate core level, $\lambda^i_s(E^i_s)$ is the inelastic mean free path of substrate photoelectrons in substrate, $\theta_s$ is the angle of emission of substrate photoelectrons with respect to the substrate-carbon interface, $E^i_s$ is the kinetic energy of substrate photoelectrons from ith energy level, hv is the x-ray energy, and z is the depth into the sample with z=0 taken to be the carbon-substrate interface in FIG. 1. See Briggs, D. and M. P. Seah, eds., *Practical Surface Analysis by Auger and X-ray Photoelectron Spectroscopy*, John Wiley & Sons, Ltd., 1983, p 197, equation (5.14), incorporated herein by reference.

The efficiency of the electron detector and the instrumental transmission function have been omitted since we are determining the number of photoelectrons emitted from the sample, rather than the number detected by the spectrometer.

Performing the z integration yields:

$$n^i_s = N_s J_0 \sigma^i_s(hv)\lambda_s(E^i_s)\sin\theta_s \qquad (6)$$

This is the total number of substrate photoelectrons crossing the interface from substrate to carbon from the ith energy level of substrate into an angle θ, φ.

Equation (6) must be integrated over all forward directed angles of emission, $\theta_s$ and $\phi^s$, from the substrate using the differential element of solid angle $\cos\theta_s d\theta_s d\phi_s$. This yields:

$$n^i_s = N_s J_0 \sigma^i_s(hv)\lambda_s(E^i_s)\pi \qquad (7)$$

Equation (7) represents the total substrate electron yield from the ith energy level that enters the carbon overlayer. To obtain the total number of substrate photoelectrons capable of causing a carbon Auger transition one sums over all states, i, with kinetic energy greater than the binding energy of C1s (285 eV).

The Auger emission produced from a carbon layer of thickness d by the total incident electron flux $n_s$ is given by:

$$I^e_{CKVV}=N_C n_s \sigma_{CKVV}(E^i_s)T(E_{CKVV})D)$$
$$(E_{CKVV})\int_{z=0}^{d}\exp[-z/\lambda_C(E_{CKVV})\sin\theta_C dz \qquad (8)$$

where $\sigma_{CKVV}(E^i_s)$ is the cross-section for carbon Auger emission upon bombardment by electrons from the ith substrate core level, $\lambda_C(E_{CKVV})$ is the inelastic mean free path of carbon Auger electrons in carbon, $\theta_C$ is the angle of emission of carbon Auger electrons with respect to the sample surface, and $E_{CKVV}$ is the kinetic energy of carbon Auger electrons. Z=0 is taken as the surface of the carbonaceous overlayer in FIG. 1. See Briggs, D. and M. P. Seah, eds., *Practical Surface Analysis* by Auger and *X-ray Photoelectron Spectroscopy*, John Wiley & Sons, Ltd., 1983, p 186, equation (5.6), incorporated herein by reference.

Integration of Equation (8) with respect to z yields the equation describing the total substrate photoelectron excited CKVV signal:

$$I^e_{CKVV}=N_C n_s \sigma_{CKVV}(E^i_s)T(E_{CKVV})D(E_{CKVV})\lambda_C(i\ E_{CKVV})\sin\theta_C\{1-\exp[-d/\lambda_C(E_{CKVV})\sin\theta_C\} \qquad (9)$$

Equation (9) can be viewed as the product of $n_s$ the substrate photo emission, the response of the carbonaceous overlayer to the substrate photoelectrons—$N_C\sigma_{CKVV}(E^i_s)$ the instrumental response—$T(E_{CKVV})D(E_{CKVV})$, and a function representing the attenuation of the carbon Auger electrons in the overlayer. Energy loss of substrate photoelectrons in the overlayer has been ignored in this analysis. For overlayer thicknesses considered in this disclosure (less than 5 nm), this energy loss is small.

The ratio $I_{CKVV}^e/I_{CKVV}^x$—i.e., the ratio of Equation (9) to Equation (3)—is Equation (2), namely:

$$\frac{I^e_{CKVV}}{I^x_{CKVV}} = \frac{\pi N_s \sigma^i_s(hv)\lambda_s(E^i_s)\sigma_{CKVV}(E^i_s)}{\sigma_{CKVV}(hv)} \qquad (2)$$

Predictions of the Substrate Effect Model

The inventors calculated the ratio $I_{CKVV}^e/I_{CKVV}^x$ using the Ebel model and the inventive Substrate Effect Model for a 2 nm thick carbonaceous layer on various substrates. The inventive Substrate Effect Model prediction was obtained by summing Equation (2) over all substrate transitions capable of causing ionization of a carbon atom in the overlayer. This includes emission of photoelectrons and Auger electrons from the substrate. The calculations were performed using a program written in BASIC, further discussed hereinbelow.

The empirical expression derived by Casnati et al. for the ionization cross-section by electrons, $\sigma_{CKVV}(E^i_s)$, has been used in this work. See the following paper incorporated herein by reference: Casnati, E., A. Tartari and C. Baraldi, "An Empirical Approach to K-Shell Ionisation Cross Section by Electrons." *Journal of Physics B: Atomic Molecular Physics* 15 (1982): 155–167. The Institute of Physics.

The Casnati expression has been found to provide accurate prediction of cross-section data for low incident electron energies. See the following paper incorporated herein by reference: Powell, C. J., "Inner-Shell Ionization Cross Sections," in Microbeam Analysis. J. Michael and P. Ingram, eds., pp 13–20, San Francisco Press, Inc., San Francisco, Calif., 1990.

The cross-section for carbon Auger emission by x-ray excitation, $\sigma_{CKVV}(hv)$, was taken to be 0.997 times $\sigma_{C1s}(hv)$, the photoionization cross-section. See Krause, M. O.

"Atomic Radiative and Radiationless Yields for K and L Shells." *J. Phys. Chem. Ref.* Data 8 (No. 2, 1979): 307–327, incorporated herein by reference; see also Scofield, J. H. "Hartree-Slater Subshell Photo ionization Cross-Sections at 1254 and 1487 eV." *Journal of Electron Spectroscopy* and *Related Phenomena* 8 (1976): 129–137, incorporated herein by reference.

Carbon Auger emission excited by x-ray fluorescence from substrate atoms was negligible for the substrate materials and x-ray excitation energy used in this work. Values of the inelastic mean free paths were taken from the work of Tanuma, et al. in which IMFP's were calculated from experimental optical data and fit to a modified Bethe equation. See Tanuma, S., C. J. Powell, D. R. Penn. "Calculations of Electron Inelastic Mean Free Paths. Part II. Data for 27 Elements over the 50–2000 eV Range." *Surface and Interface Analysis* 17 (1991): 911–926.

Figure 2:
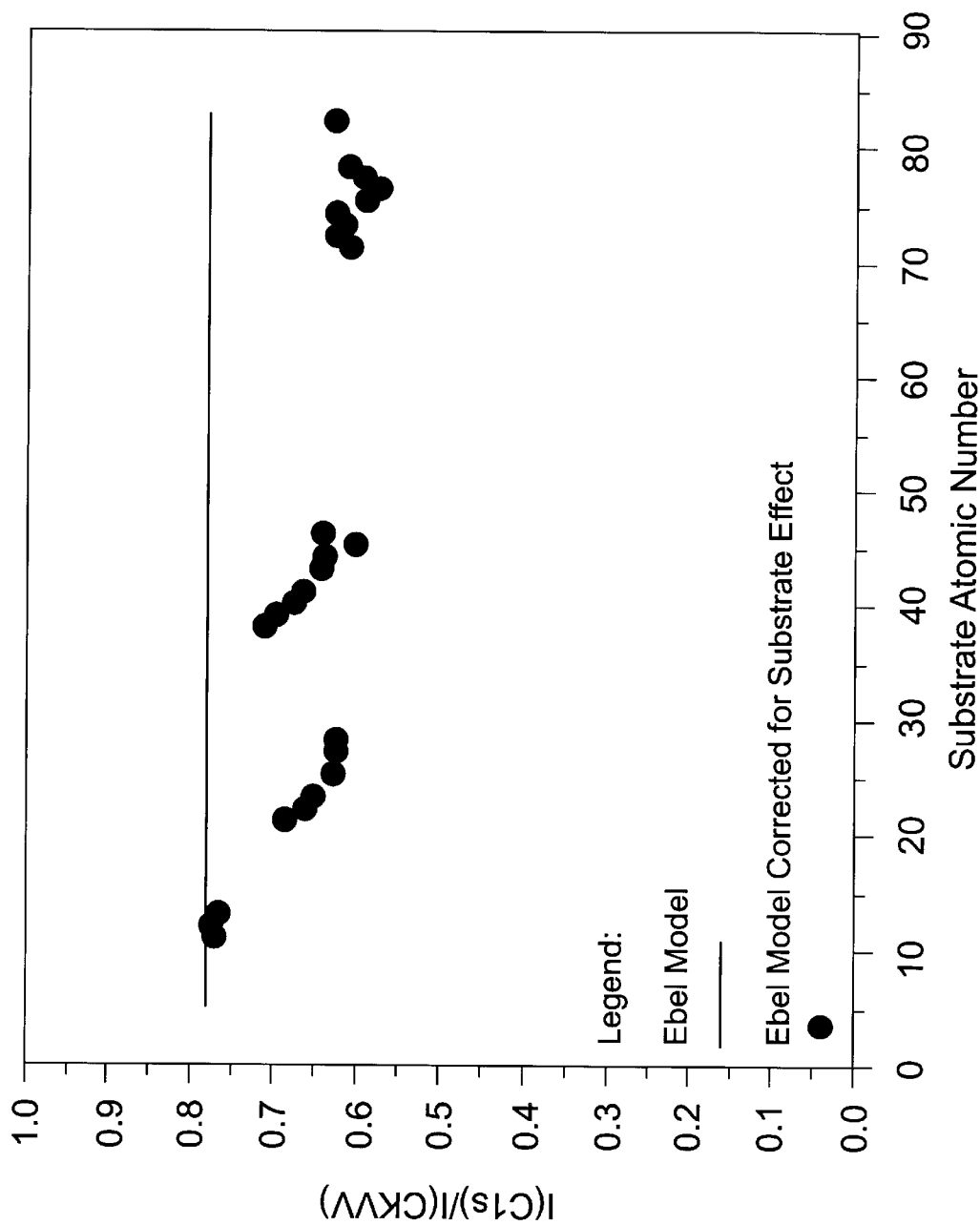
FIG. 2 is a plot of carbon 1s to carbon CKVV peak area ratios predicted by the Ebel Model and the inventive Substrate Effect Model versus substrate atomic number.
Figure 3A:
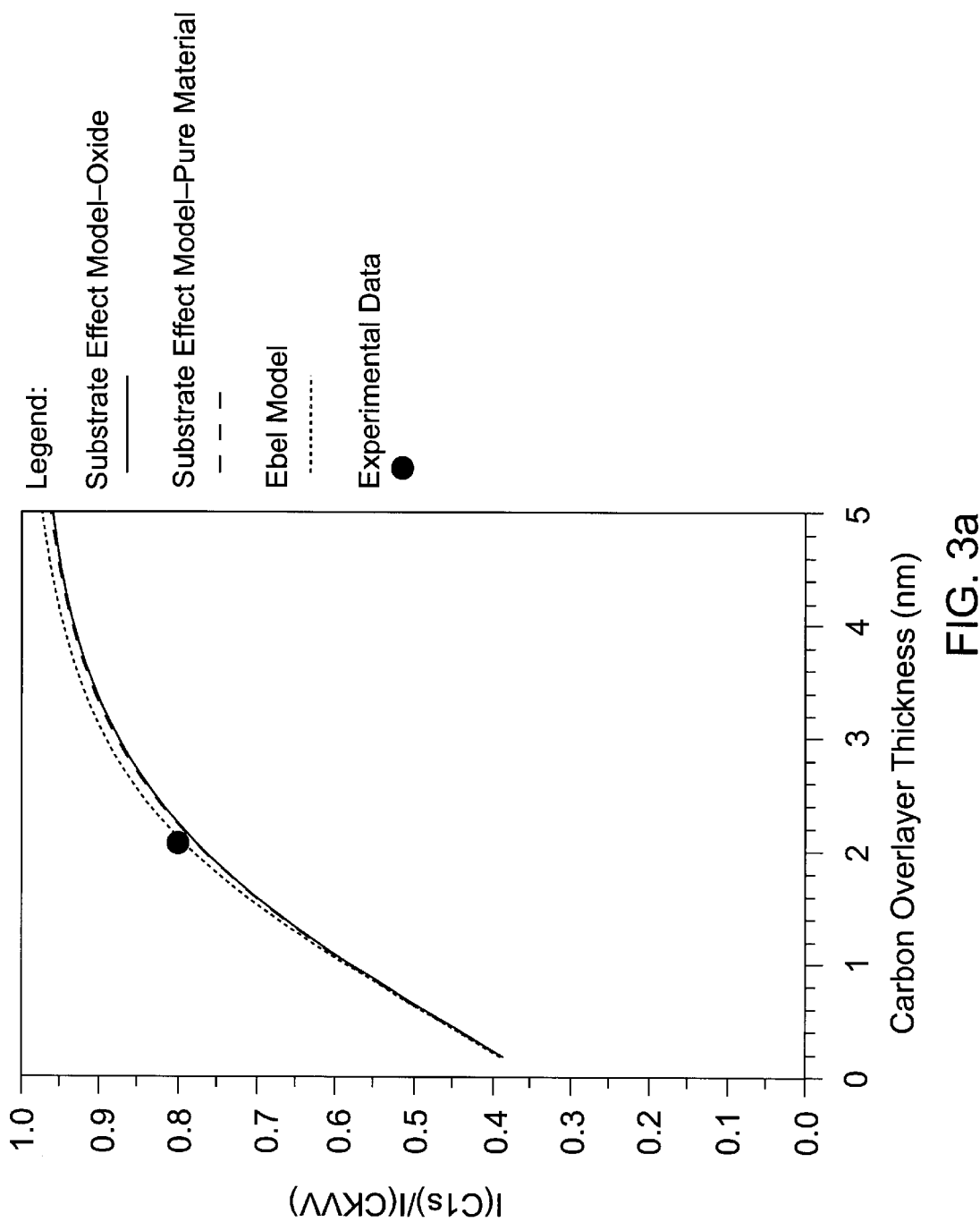
FIG. 3a through FIG. 3f are plots of carbon 1s to carbon CKVV peak area ratios predicted by the Ebel Model, the inventive Substrate Effect Model, and determined by experiment versus overlayer thickness for the following substrates: aluminum (FIG. 3a); silicon (FIG. 3b); titanium (FIG. 3c); copper (FIG. 3d); silver (FIG. 3e); and gold (FIG. 3f). Substrate Effect Model results are displayed for both elemental substrates and oxides.
Figure 3B:
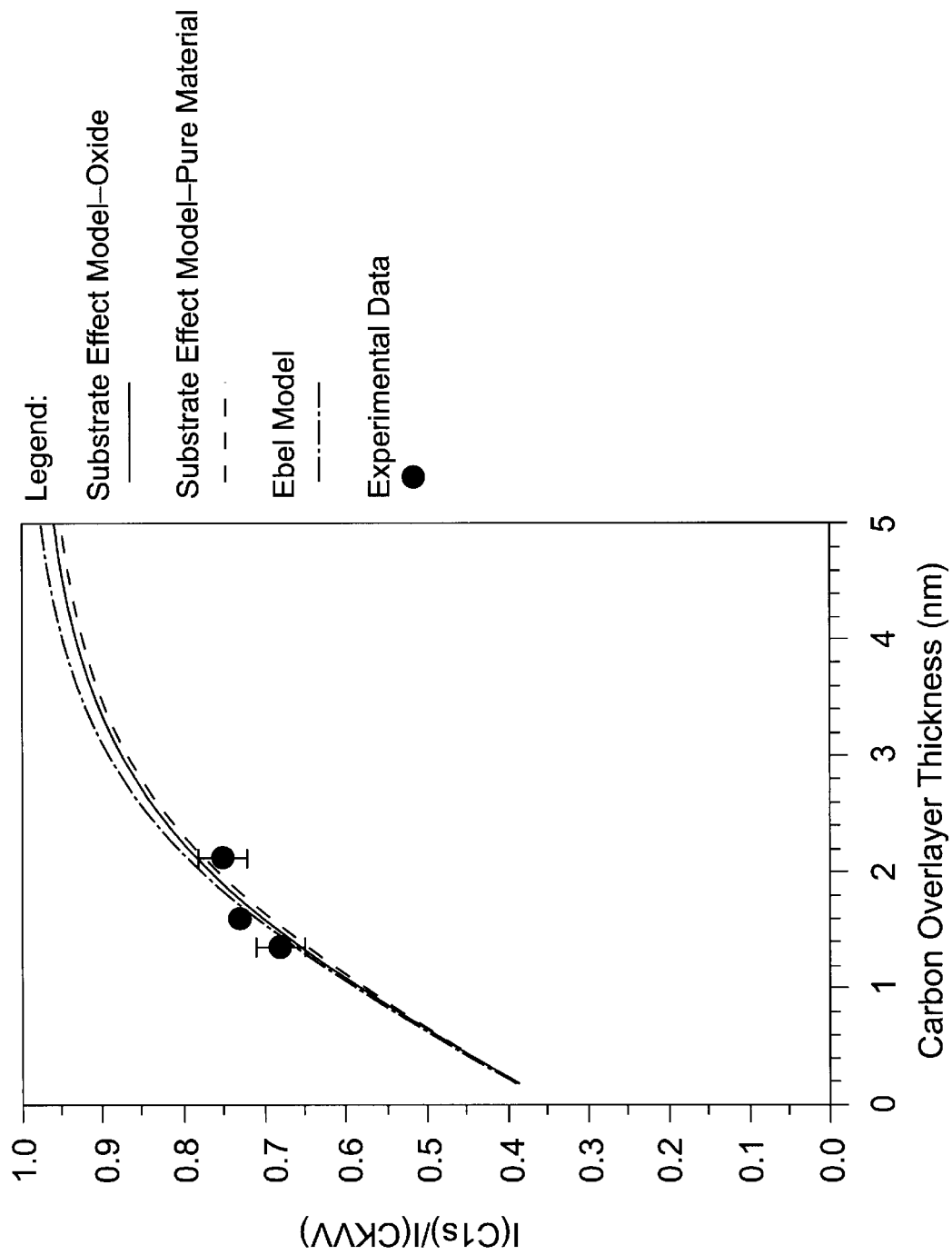
Figure 3C:
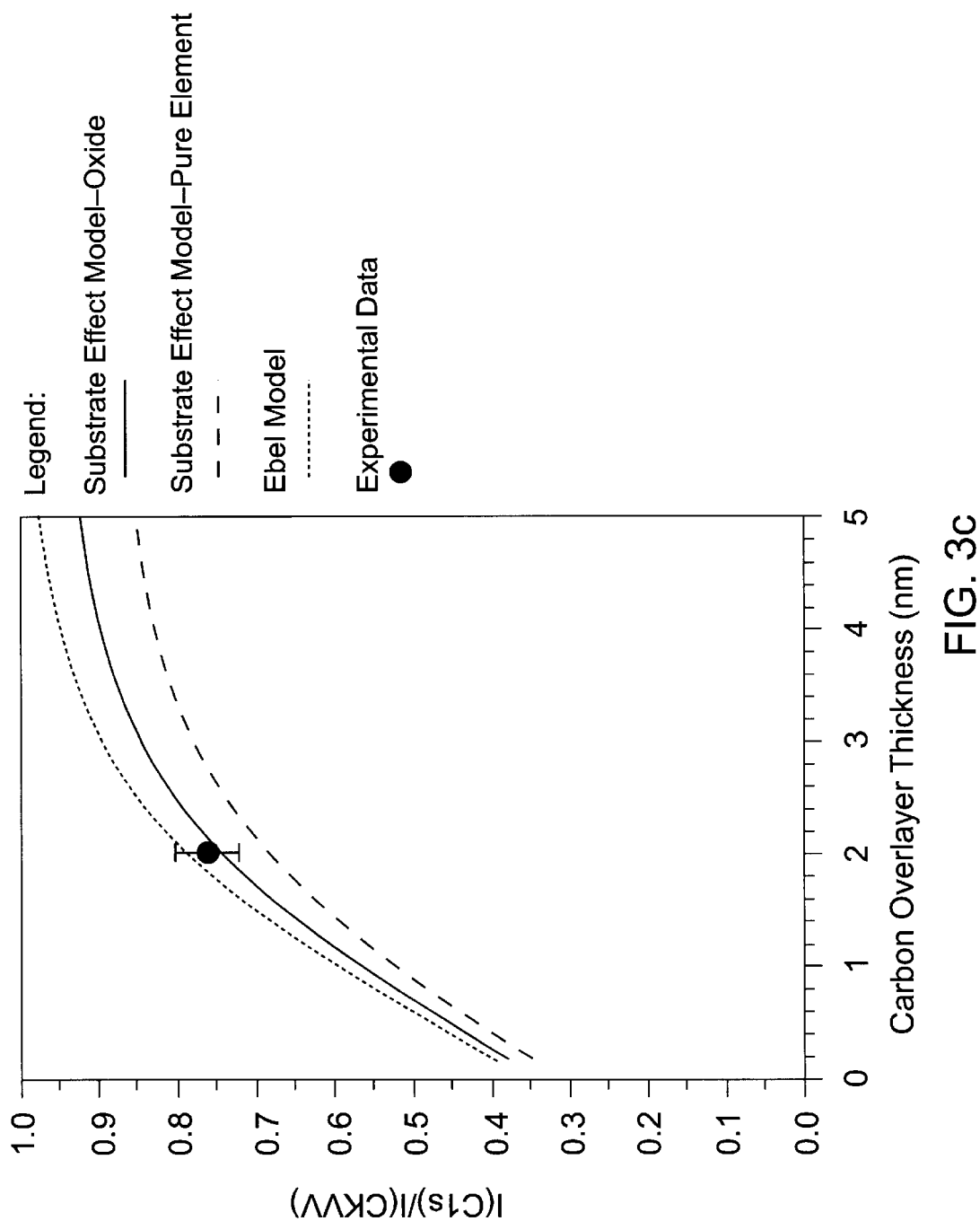
Figure 3D:
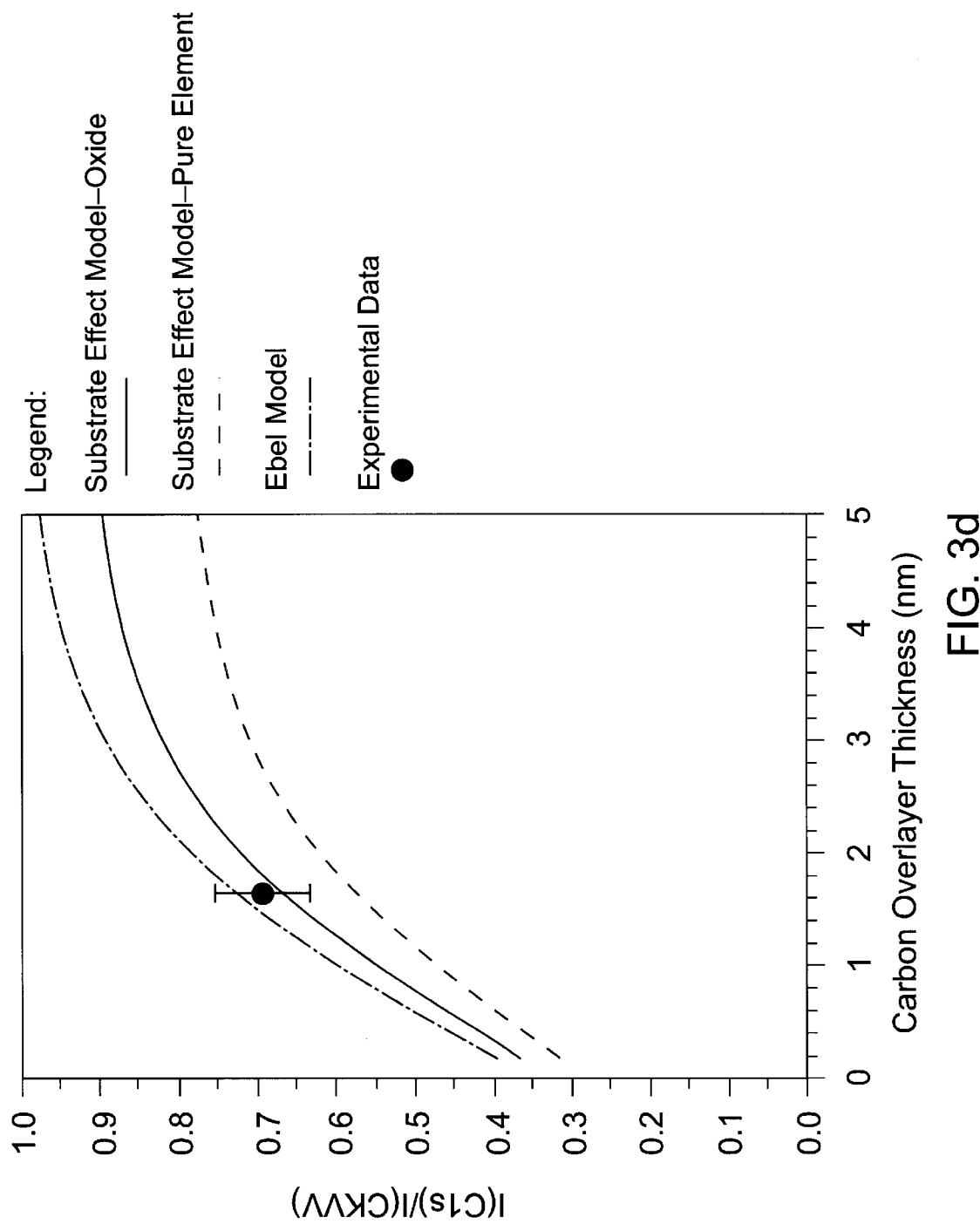
Figure 3E:
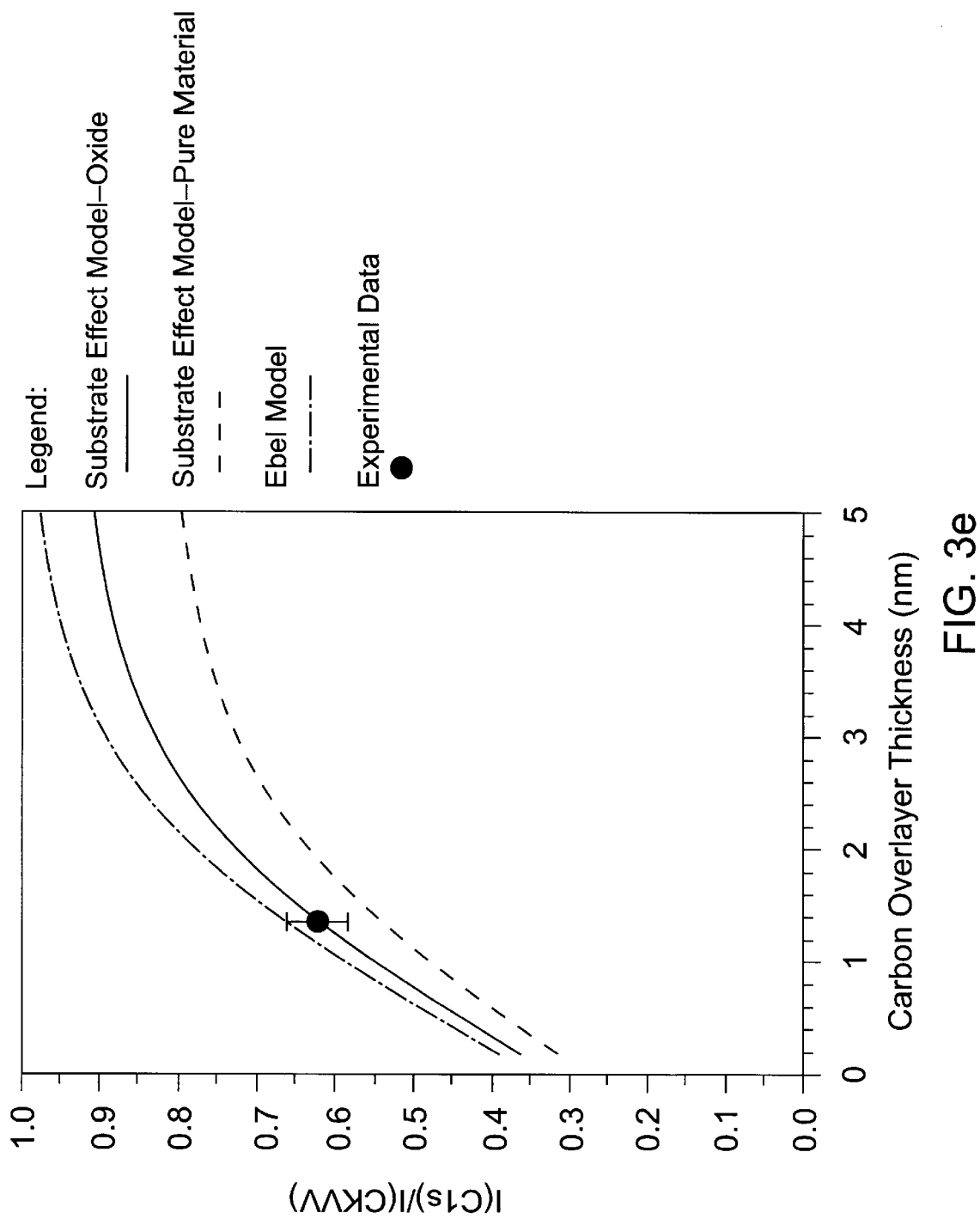
Figure 3F:
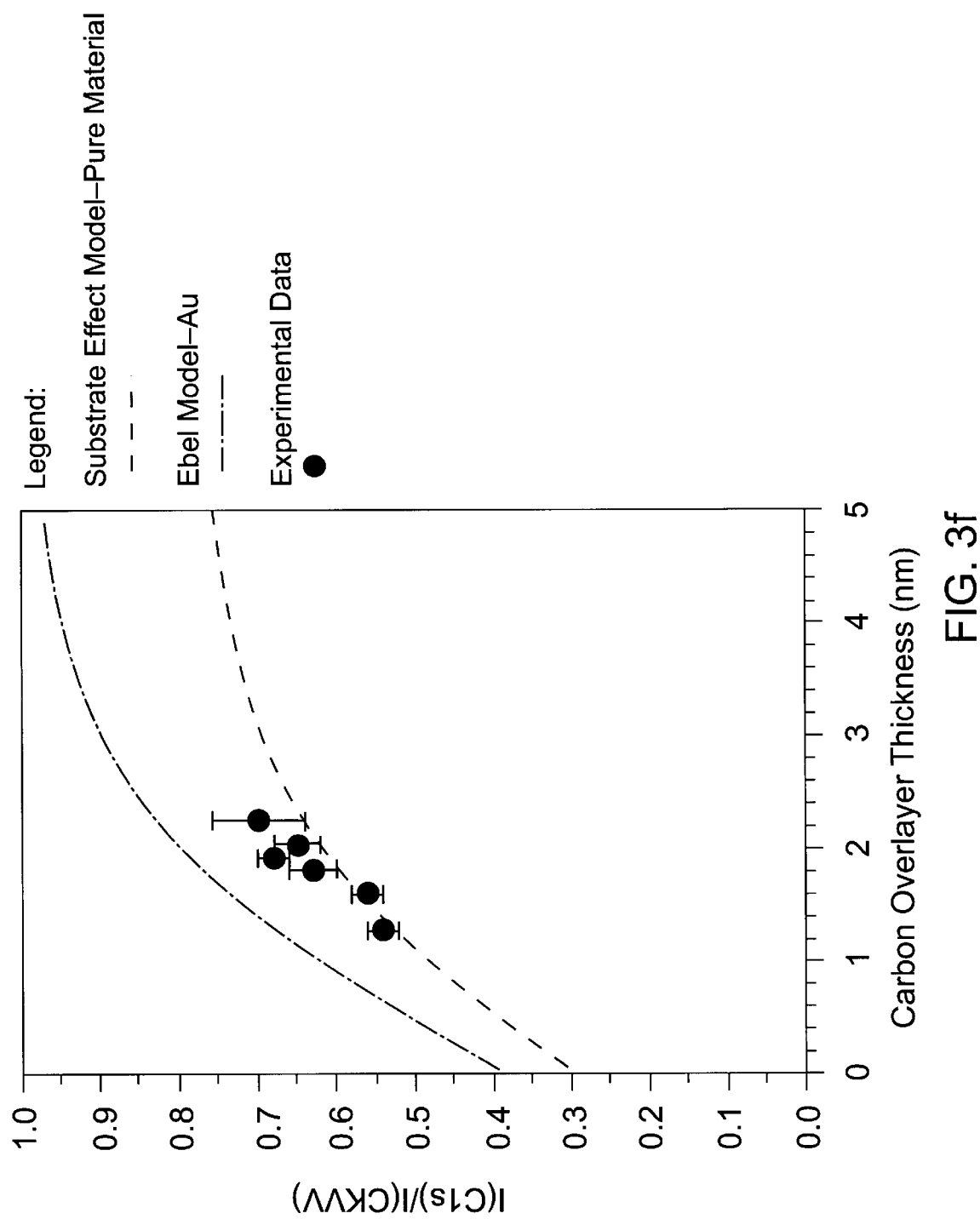

With reference to FIG. 2, predicted $I_{C1s}/I_{CKVV}$ ratios for the Ebel and inventive Substrate Effect Models for a 2 nm thick carbonaceous overlayer on various substrates are shown in FIG. 2. A detection angle, $\theta_C$, of 30° with respect to the surface plane was used in this calculation.

FIG. 2 demonstrates that the general trend is a decrease in $I_{C1s}/I_{CKVV}$ with increasing atomic number. Superimposed on this trend are variations in $I_{C1s}/I_{CKVV}$ caused by the effect of substrate photoelectron energy on carbon excitation cross-section $\sigma_C(E_s^i)$ and IMFP within the carbon layer. FIG. 2 demonstrates that the inventive Substrate Effect Model is very similar to the Ebel Model for low atomic number substrates, but is appreciably different for higher atomic number substrates.

Equation (2) demonstrates that the enhancement in the CKVV signal predicted by the inventive Substrate Effect Model depends linearly on $n_s^i$, the photoelectron emission from the substrate. Thus, the large number of photoelectrons from high Z substrates increases the flux of carbon Auger electrons emitted from the carbonaceous layer. This increases the CKVV signal observed with XPS; the C1s signal is not affected because the substrate photoelectrons exciting the C1s photoelectrons vary in energy. Thus, for most high Z substrates, the $I_{C1s}/I_{CKVV}$ ratio predicted by the inventive Substrate Effect Model is less than that predicted by the Ebel Model.

Reference is now being made to FIG. 3a through FIG. 3f, which depict the carbon 1s to carbon KVV ratio predicted by the Ebel Model and the inventive Substrate Effect Model for a carbonaceous overlayer on six different substrates (aluminum, glass, titanium, copper, silver, and gold, respectively) as a function of overlayer thickness.

The inventive Substrate Effect Model predicts a lower $I_{C1s}/I_{CKVV}$ ratio than the Ebel Model for a given overlayer thickness; the exact difference between the two models depends on the substrate material and the overlayer thickness.

It can again be seen that the difference in $I_{C1s}/I_{CKVV}$ is quite large between the two models for higher Z substrates such as titanium, copper, silver and gold, due to their large photo ionization cross-section.

It can also be seen from FIG. 3a through FIG. 3f that there is little difference between the Ebel Model and the inventive Substrate Effect Model for the lower Z substrates, glass and Aluminum.

BASIC Program for Calculating the Substrate Effect

The program outputs an ASCII file containing four columns: overlayer thickness in nm; the Ebel Model result for $I_{C1s}/I_{CKVV}$ for that layer thickness; the substrate effect correction factor—$(1+I_C^e/I_C^x)$ (the ratio of equations 9 to 3); and, the $I_{C1s}/I_{CKVV}$ ratio determined from the Substrate Effect Model. Within this calculation numerous tabulated values and relations were employed, as previously discussed herein.

The program requires the following inputs: substrate density; molecular weight; plasmon energy; the beta, gamma, C and D terms in the modified Bethe formalism; and, the kinetic energies and photo ionization cross-sections of the substrate energy levels with kinetic energy greater than 285 eV. The data is inputted to the program in an ASCI file with the following format:

substrate density substrate molecular weight substrate plasmon energy

Bethe beta term

Bethe gamma term

Bethe C term

Bethe D term number of substrate transitions atomic fraction of oxygen in the substrate (i.e., $TiO_2$ would be 0.67)

photoelectron kinetic energy of first substrate transition photo ionization cross-section of first substrate transition flag indicating whether transition #1 is an oxygen transition (1) or not (0)

photoelectron kinetic energy of last substrate transition photo ionization cross-section of last substrate transition flag indicating whether last transition is an oxygen transition (1) or not (0).

The program listing is as follows:

```
5 CLS
6 ' OVERAN10
10 PRINT "Program to calculate the correction factor to the Ebel Model"
20 PRINT "in the case of an overlayer on some homogeneous substrate."
25 'Bruce C. Beard and Robert A. Brizzolara, 1/96–11/97
26 'This version accounts for oxides
30 '
40 DIM sym$(20), en(20), sco(20), oflag(20), lamc(20), lamz(20), R(20), Qk(20), rsum(100), Ebel(100)
50 pi=3.1415926#
60 ao=5.2918E-09 ' cm units Bohr radius
61 '
65 INPUT "Enter the name of the file containing the input parameters"; NF$
70 'This file should contain substrate density, atomic weight and plasmon energy,
75 'TPP Beta, Gamma, C, D terms, number of transitions, energy level and cross section
80 'for each transition, each on its own line
85 ' Obtain values for Bethe coefficients and plasmon energy from
90 ' Tanuma, SIA 17, p.911 (1991) Tables 1 and 3
95 NF$="d:\projects\substrat\model"+NF$
100 OPEN "I", #1, NF$
105 INPUT #1, dens
110 INPUT #1, mw
115 INPUT #1, eplas
120 atdens=6.023E+23*dens/mw
125 INPUT #1, beta
130 INPUT #1, gamma
135 INPUT #1, cterm
140 INPUT #1, dterm
```

```
145 INPUT #1, num
146 INPUT #1, o2percent
150 FOR i=1 TO num STEP 1
155 INPUT #1, en(i)
160 INPUT #1, sco(i)
161 INPUT #1, oflag(i)
165 NEXT i
166 CLOSE #1
167 '
180 PRINT "Emission angle is measured relative to the surface plane."
185 INPUT "Enter the emission angle from surface, degrees:", surfang
190 surfrad=surfang*pi/180
201
202 laythick=0
203 al%=0
210 laythick=laythick+.1 'layer thickness in nm
211 z=laythick*.0000001' puts layer thickness into units of cm
212 rsum=0
213 al%=al%+1
220 '
230 'The following For/Next loop steps thru the substrate energy levels
240 FOR i=1 TO num STEP 1
245 '
250 'Calculate IMFP's for Z (substrate) and C in units of cm using the Modified
260 'Bethe eqn. approach, SIA, vol 17, 911 & 927, 1991
270 lamc(i)=en(i)*1E-08/(497.3*(.0159*LOG(.117*en(i))−(.905/en(i))+(18.4/(en(i))^2)))' cm units
280 lamz(i)=en(i)*1E-08/((eplas ^2)*(beta*LOG(gamma*en(i))−(cterm/en(i))+(dterm/(en(i))^2)))' cm units
295 '
300 ' Calculate cross-section for C excited by substrate electrons using the Casnati
310 ' relation code. Assume that Zk is the # of e- in the K-shell which for
311 ' C is 2. Assume that F (relativistic correction) in this case is 1.
316 u=en(i)/285
317 d=−.0318+(.316/u)−(.1135/(u^2))
318 phi=10.57*EXP((−1.736/u)+(.317/(u^2)))
320 psi=(285/13.06)^d
330 qe2=(2*(ao^2)*(13.06^2)*psi*phi*LOG(u))/u
340 Qk(i)=qe2/(285 ^2) 'in units of cm^2, electron excited CKVV cross-section
490 '
550 'Calculate the substrate effect correction factor
560 '.997 in denom below is x-ray cross-section for CKVV
570 IF o2percent>0 AND oflag(i)=1 THEN atfract=o2percent
580 IF o2percent>0 AND oflag(i)=0 THEN atfract=(1−o2percent)
585 IF o2percent=0 THEN atfract=1
586 IF o2percent<0 OR o2percent>1 THEN PRINT "input error−o2percent": END
587 ' PRINT o2percent, oflag(i), atfract
590 R(i)=(pi*atfract*atdens*sco(i)*lamz(i)*Qk(i))/.997
610 rsum(al%)=rsum(al%)+R(i) 'This is the correction factor
620 NEXT i
621 '
625 ' Ebel Model calculation, Carbon IMFPs are 2.7/1.0
630 Ebel(al%)=((1−EXP(−laythick/(2.7*SIN(surfrad))))/(1−EXP(−laythick/(1*SIN(surfrad))))) 'Eqn 1
685 IF laythick>5 GOTO 700
690 GOTO 210
700 PRINT "Write results to disk ?"
710 INPUT "yes=1, no=2, ?", yn
715 IF yn=2 GOTO 750 ELSE GOTO 720
720 INPUT "File name"; file$
721 file$="d:projects\substrat\model"+file$
725 OPEN "O", #1, file$
730 FOR i=1 TO al%
735 WRITE #1, i/10, Ebel(i), rsum(i), Ebel(i)/(1+rsum(i)): NEXT i
740 CLOSE #1
750 PRINT "calculate again with same substrate but differing emission angle ?"
760 INPUT "yes=1, no=2, ?", yn
770 IF yn=1 GOTO 180 ELSE GOTO 900
900 STOP
```

Experimental Verification of the Substrate Effect

Still referring to FIG. 3a through FIG. 3f, reference is also being made to the table which is designated FIG. 4. To test the predictions of the inventive Substrate Effect Model, the inventors measured the carbon 1s and carbon Auger peak intensities from carbonaceous overlayers of precisely controlled thickness on glass, aluminum, titanium, copper, silver and gold substrates. These substrates are predicted by the inventive Substrate Effect Model to have a wide variation in substrate-excited carbon Auger electron emission.

The following six sets of samples were employed: (1) a set of alkane-thiol self-assembled monolayers on gold; (2) a set of alkyltrichlorosilane self-assembled monolayers on glass; (3) a Langmuir-Blodgett film of hexadecanoic acid on titanium; (4) a 10-carbon chain hydroxamic acid monolayer on silver; (5) a 14-carbon chain carboxylic acid monolayer on aluminum; and, (6) a 12-carbon chain amine on copper.

(a) XPS Data Acquisition

XPS data were acquired using two different spectrometers: a Physical Electronics 5400 and a Physical Electronics 5600. Spectra were excited with Mg K$\alpha$ x-rays (1253.6 eV). Angle dependent XPS analysis was performed to verify overlayer thickness. ADXPS data were collected at five angles ranging from 15 to 80 degrees (relative to the surface plane). C1s and CKVV peaks were collected at each angle: Data collected at thirty degrees relative to the surface plane were used for the C1s/CKVV ratio data treatment.

Care was taken to keep the cumulative x-ray dose to a minimum to abode desorption of the overlayer; therefore, the instrumental resolution was intentionally set low to speed collection (pass energies of 178 eV and 187 eV were employed on the 5400 and 5600 systems respectively). Data collection time was less than eight minutes per sample resulting in no observable change in the carbon signal from the carbon overlayer.

Areas under the CKVV and C1s were determined by curve fitting with a minimum number of components to achieve a good representation of the experimental data. No emphasis was placed on physical realism for these fits. Constant end point values were used for the regions from which a linear background was determined.

(b) Sample Preparation

The substrate preparation and monolayer formation were performed in the ambient, except where noted otherwise.

(i) Alkanethiols

Gold substrates were prepared following the procedure given by Ulman. See Ulman, A., *An Introduction to Ultrathin Organic Films*, Academic Press, New York, New York, 1991, p 280.

Approximately 200 nm of gold was sputter-deposited onto freshly cleaved mica. Alkane thiols {$CH_3(CH_2)_{15}SH$}

(Aldrich Chemical Co.) were used as received. The alkane thiol was diluted 1:125 in isopropyl alcohol (Fisher Scientific, Optima grade). The gold-on-mica substrates were immersed in the thiol solution at room temperature for approximately 24 hours resulting in a uniform single overlayer of the alkane thiol.

The substrates were rinsed thoroughly with isopropyl alcohol upon removal from the thiol solution. Additional hexadecane-thiol-on-gold samples were graciously supplied by the group of M. Porter at Iowa State University. This set of samples used goldcoated glass substrates.

(ii) Langmuir-Blodgett Films The Langmuir-Blodgett samples were generously supplied by Dr. Bill Barger, Naval Research Laboratory. The films were deposited on titanium using standard LB techniques, from a solution of 1.2264 mg/ml hexadecanoic acid in benzene. The titanium substrates, Alfa 99.96%, were washed in 20% sulfuric acid in water, then rinsed in distilled water prior to film deposition.

(iii) Silanes The silane-based self-assembled monolayer were prepared following published procedures. See Stenger, D, J. Georger, C. Dulcey, J. Hickman, A. Rudolph, T. Nielson, S. McCort, J. Calvert. *J. Am. Chem. Soc.* 114, 8435–8442 (1992).

Glass coverslips (Corning Glass Works, Corning, NY) were immersed in 50:50 HCl:MeOH for approximately 30 minutes, and then in boiling distilled water for approximately 30 minutes. The substrates were then baked at 150° C. for 2 hours to remove residual water.

Silanization was done in a nitrogen-filled glovebag. The hexadecyl trichlorosilane was diluted to 5% in hexane (Sigma-Aldrich, HPLC grade).

Following silanization, the coverglasses were rinsed thoroughly with hexane. Outside the glovebag, the coverglasses were rinsed with isopropanol (Fisher), baked at 120° C. for 5 minutes, and rinsed again with isopropanol. The advancing contact angles of the silanized coverglasses were 95–100°.

(iv) Preparation of Monolayer on Copper, Silver and Aluminum

Each of these substrates was prepared from 99.99% metal foils, obtained from Alfa. The surfaces were mechanically polished to a final grit size of 0.3 micron to remove the bulk surface oxide. The copper and silver foils were chemically cleaned in dilute $H_3PO_4$ for 30 seconds, and then cleaned ultrasonically in distilled water.

All substrates were then cleaned ultrasonically in methanol, isopropanol and then heptane to remove residual surface organic layers. Copper and aluminum substrates were permitted to form air stable oxides by exposure to ambient for 30 minutes prior to immersion in the self-assembly solution.

Preparation of the dodecylamine (Aldrich) monolayer on copper followed the procedures described in papers by Chen et al., and McDevitt et al. See Chen, K., C. Mirkin, R. Lo, J. Zhao, J. McDevitt. *J. Am. Chem. Soc.* 117, 6374 (1995). See also McDevitt, J., C. Mirkin, R. Lo, K. Chen, J. Zhou, F. Xu, S. Haupt, J. Zhao, D. Jurbergs. *Chemistry of Materials* 8, 811 (1996).

The $C_{10}$ hydroxamic acid was graciously supplied by the group of G. Whitesides, Harvard University, Cambridge Mass. Procedures for the preparation of hydroxamic acid layers on silver are described in a paper by this group. See Folkers, J., C. Gorman, P. Laibinis, S. Buchholz, G. Whitesides, R. Nuzzo. *Langmuir* 11(3), 813 (1995).

Fatty acid ($C_{14}$, R—COOH, Aldrich) monolayer on the aluminum surface were prepared following the descriptions provided in the papers by Laibinis et al. and Y. T. Tao. See Laibinis, P., J. Hickman, M. Wrighton, G. Whitesides. *Science* 245, 845 (1989). See also Tao Y. T. *J. Am. Chem. Soc.* 115, 4350 (1993).

(c) Experimental Results

The inventors compared the measured $I_{C1s}/I_{CKVV}$ ratio to those predicted by the Ebel and inventive Substrate Effect Models. These results are reported in FIG. 4.

FIG. 4 reports the overlayer thickness, measured $I_{C1s}/I_{CKVV}$ ratio, the $I_{C1s}/I_{CKVV}$ ratio calculated from the Ebel Model, the substrate effect correction $(1+I_c^e/I_c^x)$, and the $I_{C1s}/I_{CKVV}$ ratio calculated from the inventive Substrate Effect Model for the various substrates assuming pure substrates (and overlayer thicknesses experimentally examined as disclosed herein). The error bars on the experimental data represent standard deviations of the mean, and were determined from the following data: aluminum and silver—two runs each on the Phi 5600 spectrometer; copper—three runs using the Phi 5600 spectrometer; titanium—one run each on the Phi 5400 and 5600 spectrometers; glass—five runs on the Phi 5400 spectrometer; gold—either three runs on the Phi 5400 spectrometer or one run each on the Phi 5400 and 5600 spectrometers.

The results reported in FIG. 4 demonstrate a general improvement between the measured $I_{C1s}/I_{CKVV}$ ratios and the inventive Substrate Effect Model predictions, compared with the Ebel Model predictions. This is most evident for the gold substrate, as would be expected due to its large photoionization cross-section. This is further illustrated in FIG. 3a through FIG. 3f which, in addition to the model results discussed previously, also show the experimental data. The error bars represent standard deviations of the mean.

For several of the low Z metals considered, the substrate effect correction appears too large. This is because the surfaces for aluminum, titanium, copper and silver are actually oxides under the ambient preparation conditions employed, and glass is a bulk oxide. In this case, the appropriate substrate effect correction must be based on the weighted emission cross-section of both metal and oxygen transitions. FIG. 4 summarizes the substrate effect results calculated in this way.

Correlation between the measured $C_{C1s}$ and $I_{CKVV}$ and the inventive Substrate Effect Model for $TiO_2$, CuO and AgO is clearly improved relative to the pure metal calculations. The correlation of the silicon and aluminum results is practically unaffected by consideration of the oxide because the substrate effect is so small for these elements. Plots for the oxide results obtained from the inventive Substrate Effect Model are shown in FIG. 3a through FIG. 3f.

The experimental data agree with the inventive Substrate Effect Model very well for all substrates when the calculations reflect the true chemical composition of the interface. In contrast, the agreement between the experimental data and the Ebel Model is poor for the gold substrate and good for low Z substrates. For the lower Z substrates, both the Ebel Model and the inventive Substrate Effect Model agree with the experimental data.

Determination of Overlayer Thickness using the Substrate Effect Model

These experimental data provide a strong demonstration that the inventive Substrate Effect Model is an accurate representation of the photo emission from the sample depicted in FIG. 1, for substrates of all compositions. Therefore, the inventive Substrate Effect Model can be employed to determine carbonaceous overlayer thicknesses, from $I_{C1s}/I_{CKVV}$ data.

In inventive practice, the application of the inventive Substrate Effect Model as described herein would generally include the following steps:

1. Determine the K constant by measuring the $I_{C1s}/I_{CKVV}$ ratio on specimen of bulk carbon (e.g., high-density polyethylene or graphite).
2. Under conditions identical to the conditions for step number 1, collect a survey scan on the sample of interest. In particular, the pass energy, analysis area and source to sample separation must be identical.
3. From the survey results, identify the approximate composition of the substrate (exclude carbon), assuming homogeneous surface structure. With this composition calculate the appropriate value for $(I_{CKVV}^e/I_{CKVV}^x)$ from Equation (2).
4. From the CKVV and C1s areas in the survey scan, determine the $I_{C1s}/I_{CKVV}$ ratio, and normalize using K determined in step number 1.
5. Using the Substrate Effect Model, [{Ebel model}×(1/(1+$(I_{CKVV}^e/I_{CKVV}^x)$))], plot the $I_{C1s}/I_{CKVV}$ ratio versus layer thickness.
6. From the experimentally determined, normalized $I_{C1s}/I_{CKVV}$ ratio in step number 4 and the plot of the Substrate Effect Model in step number 5, determine the overlayer thickness.

Many inventive embodiments are directed to improving accuracy of XPS quantitative analysis. According to such inventive embodiments, the invention increases accuracy with regard to the correction of the presence of an adventitious is carbonaceous overlayer in the quantitative analysis of XPS data. Generally, such embodiments of this invention will include, in addition to steps 1 through steps 6 above, the following step number 7:

7. Accurately determine the substrate composition using the well-established overlayer/substrate equations. See Clark, D. T., A. Dilks, D. Shuttleworth and H. R. Thomas. "Angular-Dependent Studies on Same Prototype Vertically and Laterally Inhomogeneous Samples."*J. Electron Spect. Rel. Phen.* 14 (1978): 247–258, incorporated herein by reference.

In the derivation of the inventive Substrate Effect Model disclosed hereinabove, only pure materials were considered. Within the discussion of the results, the application of the inventive Substrate Effect Model to compounds at the interface was discussed. Such compounds, (e.g. oxides or alloys) can be evaluated by properly weighting the photoelectron emission with the atom density of the elements present in the compound. Such a treatment would seem to presuppose the final composition of the substrate. However, it would be sufficient to use the approximate substrate composition extracted from the survey data in the evaluation of Equation (2). In consideration of the Substrate Effect Model determination of the carbonaceous overlayer in accordance with the present invention, the substrate composition can then be refined to reflect the true composition.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. A method for determining the thickness of an overlayer which is present on a substrate, said method comprising:

effectuating x-ray photoelectron spectroscopy with respect to said overlayer, wherein said effectuating includes:

measuring the intensity of an Auger electron emission peak with respect to an element in said overlayer; and measuring the intensity of a non-Auger electron emission peak with respect to said element; and evaluating the ratio of the measured intensity of said Auger electron emission peak to the measured intensity of said non-Auger electron emission peak, wherein said evaluating includes considering said Auger electron emission peak to be attributable to the combination of: direct x-ray excitation of said substrate; and x-ray excitation of photoelectrons from said substrate;

wherein said evaluating includes solving for d in the equation $$I_{Znl}/I_{Z(A)} = \{K(1-\exp[-d/\lambda_Z(E_{Znl})\sin\theta])\}/\{(1-\exp[-d/\lambda_Z(E_{Z(A)})\sin\theta])(1+I_{Z(A)}^e/I_{Z(A)}^x)\},$$

wherein

Z represents said element;

Z(A) is said Auger electron emission peak;

Znl is said non-Auger electron emission peak;

$I_{Z(A)}$ is the intensity of said Auger electron emission peak;

$I_{Znl}$ is the intensity of said non-Auger electron emission peak;

d is said thickness of said overlayer;

$\lambda_Z(E_{Z(A)})$ is the inelastic mean free path of the Auger electrons in said element;

$\lambda_Z(E_{Znl})$ is the inelastic mean free path of the nl photoelectrons in said element;

θ is the angle of emission of photoelectrons with respect to the plane defined by said substrate;

K is a constant which is equal to the measured $I_{Znl}/I_{Z(A)}$ for an infinitely thick elemental sample;

$I_{Z(A)}^x$ is a first portion of said intensity of said Auger electron emission peak, said first portion corresponding to direct x-ray excitation of said substrate;

$I_{Z(A)}^e$ is a second portion of said intensity of said Auger electron emission peak, said second portion corresponding to photoelectron excitation from said substrate;

$[I_{Z(A)}^e/I_{Z(A)}^x]$ equals $[\pi N_s \sigma_s^i(h\nu)\lambda_s(E_s^i)\sigma_{Z(A)}(E_s^i)]$ divided by $[\sigma_{Z(A)}(h\nu)]$;

$N_s$ is the number of atoms/cm$^3$ in said substrate;

$\sigma_s^i(h\nu)$ is the cross-section for photoelectron emission from the ith core level of said substrate;

$\lambda_s(E_s^i)$ is the inelastic mean free path of substrate photoelectrons in said substrate;

$\sigma_{Z(A)}(E_s^i)$ is the cross-section for Auger emission upon bombardment by electrons from the ith core level of said substrate; and $\sigma_{Z(A)}(h\nu)$ is the cross-section for Auger emission by x-ray excitation.

2. A method for determining the thickness of an overlayer as in claim 1, wherein said element is selected from the group of elements consisting of carbon and oxygen.

3. A method for determining the thickness of a carbonaceous overlayer which is present on a substrate, said method comprising:

effectuating x-ray photoelectron spectroscopy with respect to said carbonaceous overlayer, wherein said effectuating includes:

measuring the intensity of the CKVV electron emission peak; and measuring the intensity of the C1s electron emission peak; and evaluating the ratio of the measured intensity of said CKVV electron emission peak to the measured intensity of said C1s electron emission peak, wherein said evaluating includes considering said CKVV electron emission peak to be attributable to the combination of:
direct x-ray excitation of said substrate; and
x-ray excitation of photoelectrons from said substrate,
wherein said evaluating includes considering said ratio to be representable as $I_{C1s}/I_{CKVV}$, wherein $I_{CKVV}$ equals $I_{CKVV}^x + I_{CKVV}^e$, wherein $I_{C1s}/I_{CKVV}$ equals $I_{C1s}/(I_{CKVV}^x + I_{CKVV}^e)$, wherein $I_{C1s}$ is the intensity of said C1s electron emission peak, wherein $I_{CKVV}$ is the intensity of the overall said CKVV electron emission peak, wherein $I_{CKVV}^x$ is the intensity of that part of said CKVV electron emission peak which is attributable to x-ray excitation of said substrate, and wherein $I_{CKVV}^e$ is the intensity of that part of said CKVV electron emission peak which is attributable to x-ray excitation of photoelectrons from said substrate.

4. A method for determining the thickness of a carbonaceous overlayer as in claim 3, wherein said evaluating includes considering $I_{C1s}/I_{CKVV}^x$ to equal $\{K(1-\exp[-d/\lambda_C(E_{C1s})\sin\theta])\}/\{(1-\exp[-d/\lambda_C(E_{CKVV})\sin\theta])\}$, wherein:

d is the thickness of said carbonaceous overlayer;
$\lambda_C(E_{C1s})$ is the inelastic mean free path of C1s photoelectrons in carbon;
$\lambda_C(E_{CKVV})$ is the inelastic mean free path of CKVV electrons in carbon;
$\theta$ is the angle of emission of photoelectrons with respect to the plane defined by said substrate; and
the constant K is equal to $I_{C1s}/I_{CKVV}$ for an infinitely thick carbon sample.

5. A method for determining the thickness of a carbonaceous overlayer as in claim 4, wherein said evaluating includes considering $I_{C1s}/(I_{CKVV}^x + I_{CKVV}^e)$ to be obtainable by dividing $I_{C1s}/I_{CKVV}$ by $(1 + I_{CKVV}^e/I_{CKVV}^x)$.

6. A method for determining the thickness of a carbonaceous overlayer as in claim 5, wherein said evaluating includes considering $I_{CKVV}^e/I_{CKVV}^x$ to equal $[\pi N_s \sigma_s^i(h\nu)\lambda_s(E_s^i)\sigma_{CKVV}(E_s^i)]/[\sigma_{CKVV}(h\nu)]$, wherein:

$N_s$ is the number of substrate atoms/cm$^3$;
$\sigma_s^i(h\nu)$ is the cross-section for photoelectron emission from the ith core level of said substrate;
$\lambda_s(E_s^i)$ is the inelastic mean free path of substrate photoelectrons in said substrate;
$\sigma_{CKVV}(E_s^i)$ is the cross-section for CKVV electron emission upon bombardment by electrons from the ith core level of said substrate; and
$\sigma_{CKVV}(h\nu)$ is the cross-section for CKVV electron emission by x-ray excitation.

7. A method for determining the thickness of a carbonaceous overlayer as in claim 5, wherein said evaluating includes considering $I_{C1s}/I_{CKVV}$ to equal $\{K(1-\exp[-d/\lambda_C(E_{C1s})\sin\theta])\}/\{(1-\exp[-d/\lambda_C(E_{CKVV})\sin\theta])(1+I_{CKVV}^e/I_{CKVV}^x)\}$.

8. A method for determining the thickness of a carbonaceous overlayer on a substrate, said method comprising:
determining the ratio $I_{C1s}/I_{CKVV}$, said determining including performing x-ray photoelectron spectroscopic measurement with respect to said carbonaceous overlayer; and
equating said ratio $I_{C1s}/I_{CKVV}$ with the expression $\{K(1-\exp[-d/\lambda_C(E_{C1s})\sin\theta])\}/\{(1-\exp[-d/\lambda_C(E_{CKVV})\sin\theta])(1+I_{CKVV}^e/I_{CKVV}^x)\}$;
wherein:
$I_{C1s}$ 1s the carbon is intensity;
$I_{CKVV}$ is the carbon KVV intensity;
d is the thickness of said carbonaceous overlayer;
$\lambda_C(E_{C1s})$ is the inelastic mean free path of carbon 1s photoelectrons in carbon;
$\lambda_C(E_{CKVV})$ is the inelastic mean free path of carbon Auger electrons in carbon;
is the angle of emission of photoelectrons with respect to the plane of said substrate;
K is a constant which is equal to the measured $I_{C1s}/I_{CKVV}$ for an infinitely thick carbon sample;
$I_{CKVV}^x$ is the portion of the carbon KVV intensity corresponding to direct x-ray excitation of said substrate;
$I_{CKVV}^e$ is the portion of the carbon KVV intensity corresponding to photoelectron excitation from said substrate;
$[I_{CKVV}^e/I_{CKVV}^x]$ equals $[\pi N_s \sigma_s^i(h\nu)\lambda_s(E_s^i)\sigma_{CKVV}(E_s^i)]$ divided by $[\sigma_{CKVV}(h\nu)]$;
$N_s$ is the number of substrate atoms/cm$^3$;
$\sigma_s^i(h\nu)$ is the cross-section for photoelectron emission from the ith core level of said substrate;
$\lambda_s(E_s^i)$ is the inelastic mean free path of substrate photoelectrons in said substrate;
$\sigma_{CKVV}(E_s^i)$ is the cross-section for carbon Auger emission upon bombardment by electrons from the ith core level of said substrate; and
$\sigma_{CKVV}(h\nu)$ is the cross-section for carbon Auger emission by x-ray excitation.

9. A method for determining the thickness of a carbonaceous overlayer as in claim 8, wherein said equating includes using a processor.

10. A method for determining the thickness of a carbonaceous overlayer as in claim 8, wherein said performing x-ray photoelectron spectroscopic measurement includes using a spectrometer.

11. A method for determining the thickness of a carbonaceous overlayer as in claim 8, wherein said equating includes correlating said ratio $I_{C1s}/I_{CKVV}$ with said carbonaceous overlayer thickness d.

12. Apparatus for determining the thickness of a carbonaceous overlayer which is present on a substrate, said apparatus comprising:
means for effectuating x-ray photoelectron spectroscopy with respect to said carbonaceous overlayer, wherein said effectuating includes:
measuring the intensity of the CKVV electron emission peak; and
measuring the intensity of the C1s electron emission peak; and
means for evaluating the ratio of the measured intensity of said CKVV electron emission peak to the measured intensity of said C1s electron emission peak, wherein said evaluating includes considering said CKVV electron emission peak to be attributable to the combination of:
direct x-ray excitation of said substrate; and
x-ray excitation of photoelectrons from said substrate;
wherein said evaluating includes considering said ratio to be representable as $I_{C1s}/I_{CKVV}$, wherein $I_{CKVV}$ equals $I_{CKVV}^x + I_{CKVV}^e$, wherein $I_{C1s}/I_{CKVV}$ equals $I_{C1s}/(I_{CKVV}^x + I_{CKVV}^e)$, wherein $I_{C1s}$ is the intensity of said C1s electron emission peak, wherein $I_{CKVV}$ is the intensity of the overall said CKVV electron emission peak, wherein $I_{CKVV}^x$ is that part of the CKVV electron emission peak which is attributable to x-ray excitation of said substrate, and wherein $I_{CKVV}^e$ is that part of the CKVV electron emission peak which is attributable to x-ray excitation of photoelectrons from said substrate.

13. Apparatus for determining the thickness of a carbonaceous overlayer as in claim 12, wherein said evaluating includes considering $I_{C1s}/I_{CKVV}^x$ to equal $\{K(1-\exp[-d/\lambda_C(E_{C1s})\sin\theta])\}/\{(1-\exp[-d/\lambda_C(E_{CKVV})\sin\theta])\}$, wherein:

d is the thickness of said carbonaceous overlayer;

$\lambda_C(E_{C1s})$ is the inelastic mean free path of C1s photoelectrons in carbon;

$\lambda_C(E_{CKVV})$ is the inelastic mean free path of CKVV electrons in carbon;

θ is the angle of emission of photoelectrons with respect to the plane defined by said substrate; and the constant K is equal to $I_{C1s}/I_{CKVV}$ for an infinitely thick carbon sample.

14. Apparatus for determining the thickness of a carbonaceous overlayer as in claim 13, wherein said evaluating includes considering $I_{C1s}/(I_{CKVV}^x + I_{CKVV}^e)$ to be obtainable by dividing $I_{C1s}/I_{CKVV}^x$ by $(1+I_{CKVV}^e/I_{CKVV}^x)$.

15. Apparatus for determining the thickness of a carbonaceous overlayer as in claim 14, wherein said evaluating includes considering $I_{CKVV}^e/I_{CKVV}^x$ to equal $[\pi N_s \sigma_s^i(h\nu)\lambda_s(E_s^i)\sigma_{CKVV}(E_s^i)]/[\sigma_{CKVV}(h\nu)]$, wherein:

$N_s$ is the number of substrate atoms/cm³;

$\sigma_s^i(h\nu)$ is the cross-section for photoelectron emission from the ith core level of said substrate;

$\lambda_s(E_s^i)$ is the inelastic mean free path of substrate photoelectrons in said substrate;

$\sigma_{CKVV}(E_s^i)$ is the cross-section for CKVV electron emission upon bombardment by electrons from the ith core level of said substrate; and $\sigma_{CKVV}(h\nu)$ is the cross-section for CKVV electron emission by x-ray excitation.

16. Apparatus for determining the thickness of a carbonaceous overlayer as in claim 14, wherein said evaluating includes considering $I_{C1s}/I_{CKVV}$ to equal $\{K(1-\exp[-d/\lambda_C(E_{C1s})\sin\theta])\}/\{(1-\exp[d/\lambda_C(E_{CKVV})\sin\theta])(1+I_{CKVV}^e/I_{CKVV}^x)\}$.

17. Apparatus for determining the thickness of a carbonaceous overlayer as in claim 12, wherein said means for evaluating includes a processor.

18. Apparatus for determining the thickness of a carbonaceous overlayer as in claim 12, wherein said means for effectuating includes a spectrometer.

* * * * *